(12) United States Patent
Sheehan et al.

(10) Patent No.: US 9,790,605 B2
(45) Date of Patent: Oct. 17, 2017

(54) IRIDIUM COMPLEXES FOR ELECTROCATALYSIS

(71) Applicant: Yale University, New Haven, CT (US)

(72) Inventors: Stafford Wheeler Sheehan, Tiverton, RI (US); Ulrich Hintermair, Rottendorf (DE); Julianne M. Thomsen, Colton, CA (US); Gary W. Brudvig, Orange, CT (US); Robert H. Crabtree, Bethany, CT (US)

(73) Assignee: Yale University, New Haven, CT (US)

( * ) Notice: Subject to any disclaimer, the term of this patent is extended or adjusted under 35 U.S.C. 154(b) by 607 days.

(21) Appl. No.: 14/317,906

(22) Filed: Jun. 27, 2014

(65) Prior Publication Data

US 2015/0021194 A1    Jan. 22, 2015

Related U.S. Application Data

(60) Provisional application No. 61/840,201, filed on Jun. 27, 2013.

(51) Int. Cl.
*C25B 11/04*    (2006.01)
*C02F 1/467*    (2006.01)
(Continued)

(52) U.S. Cl.
CPC ........ *C25B 11/0489* (2013.01); *C02F 1/4672* (2013.01); *C07C 303/32* (2013.01);
(Continued)

(58) Field of Classification Search
CPC ............ C25B 11/0489; C25B 11/0447; C25B 11/0405; C25B 1/003; C25B 3/02;
(Continued)

(56) References Cited

U.S. PATENT DOCUMENTS 3,897,328 A    7/1975    Mitchell
2008/0248195 A1    10/2008    Reetz
(Continued)

FOREIGN PATENT DOCUMENTS

CA    2755820    12/2009
EP    0987054    6/2004
(Continued)

OTHER PUBLICATIONS

Aime, et al., "The reaction of Co4(CO)12 with Ph2PCH2CH2PPh2. Spectroscopic identification of polymeric products", J Organomet Chem., 309:C51 (1986).
(Continued)

*Primary Examiner* — Arun S Phasge
(74) *Attorney, Agent, or Firm* — Pabst Patent Group LLP

(57) ABSTRACT

Solution-phase (e.g., homogeneous) or surface-immobilized (e.g., heterogeneous) electrode-driven oxidation catalysts based on iridium coordination compounds which self-assemble upon chemical or electrochemical oxidation of suitable precursors and methods of making and using thereof are. Iridium species such as $\{[Ir(LX)_x(H_2O)_y(\mu\text{-}O)]_z^{m+}\}_n$ wherein x, y, m are integers from 0-4, z and n from 1-4 and LX is an oxidation-resistant chelate ligand or ligands, such as such as 2(2-pyridyl)-2-propanolate, form upon oxidation of various molecular iridium complexes, for instance [Cp*Ir(LX)OH] or [(cod)Ir(LX)] (Cp*=pentamethylcyclopentadienyl, cod=cis-cis,1,5-cyclooctadiene) when exposed to oxidative conditions, such as sodium periodate ($NaIO_4$) in aqueous solution at ambient conditions.

35 Claims, 22 Drawing Sheets

(51) Int. Cl.
| | |
|---|---|
| H01M 4/92 | (2006.01) |
| C25B 1/00 | (2006.01) |
| C25B 3/02 | (2006.01) |
| C07C 309/44 | (2006.01) |
| C07C 303/32 | (2006.01) |
| C07F 15/00 | (2006.01) |
| C07F 17/00 | (2006.01) |
| C02F 1/461 | (2006.01) |

(52) U.S. Cl.
CPC ........ *C07C 309/44* (2013.01); *C07F 15/0033* (2013.01); *C07F 17/00* (2013.01); *C25B 1/003* (2013.01); *C25B 3/02* (2013.01); *C25B 11/0405* (2013.01); *C25B 11/0447* (2013.01); *H01M 4/923* (2013.01); *H01M 4/926* (2013.01); *C02F 2001/46142* (2013.01); *C02F 2303/10* (2013.01); *H01M 4/925* (2013.01); *Y02W 10/30* (2015.05)

(58) Field of Classification Search
CPC ...... C25B 11/04; C07F 17/00; C07F 15/0033; C07C 303/32; C07C 309/44; C02F 1/4672; C02F 2303/10; C02F 2001/46142; H01M 4/923; H01M 4/926; H01M 4/925
See application file for complete search history.

(56) References Cited

U.S. PATENT DOCUMENTS

| | | |
|---|---|---|
| 2012/0214084 A1 | 8/2012 | Sharman |
| 2013/0037417 A1 | 2/2013 | Jia |
| 2014/0054180 A1 | 2/2014 | Morimitsu |

FOREIGN PATENT DOCUMENTS

| | | |
|---|---|---|
| EP | 1701790 | 9/2009 |
| WO | 2009029539 | 3/2009 |
| WO | 2009154753 | 12/2009 |
| WO | 2012122605 | 9/2012 |
| WO | 2013100162 | 7/2013 |

OTHER PUBLICATIONS

Ayers, "An overview of electrochemical carbon dioxide reduction", Spec Publ-R Soc Chem., 153:365-74 (1994).
Ayres and Peiro, "Material efficiency: rare and critical metals", Philos Trans R Soc A., 371:20110563 (2013).
Blakemore, et al., "Anodic Deposition of a Robust Iridium Water-Oxidation Catalyst from Organometallic Precursors", Chem Sci., 2:94-8 (2011).
Bloomfield, et al.., "A heterogeneous water oxidation catalyst from dicobalt octacarbonyl and 1.2-bis(diphenylphospino)ethane", New J Chem., 38:1540-5 (2014).
Bockris and Otagawa, "The Electrocatalysis of Oxygen Evolution on Perovskites", J Electrochem. Soc., 131:290-302 (1984).
Cunninghame, et al., "Electron transfer in organometallic clusters, 12. Regioselective sequential electrocatalytic substitution of [.mu.-(CF3)2C2]Co2(CO)6 by polydentate ligands", Organometallics, 6:1470-9 (1987).
Dinca, et al., "Nickel-borate oxygen-evolving catalyst that functions under benign conditions", PNAS, 107:10337-41 (2010).
Erdmann and Graedel, "Criticality of non-fuel minerals: a review of major approaches and analyses", Environ Sci Technol, 45:7620-30 (2011).
Esswein, et al., "Highly active cobalt phosphate and borate based oxygen evolving catalysts operating in neutral and natural waters", Energy Environ., 4:499-(2011).
Gutowski, et al., "The energy required to produce materials: constraints on energy-intensity improvements, parameters of demand", Philos Trans R Soc A., 371:2012003 (2013).
Hintermair, et al., "Precursor transformation during molecular oxidation catalysis with organometallic iridium complexes", J Am Chem Soc., 135:10837-51 (2013).
Irshad and Munichandraiah, "EQCM Investigation of Electrochemical Deposition and Stability of Co-Pi Oxygen Evolution Catalyst of Solar Energy Storage", J Phys Chem C., 117:8001-8 (2013).
Ismail and Badawy, "Electrochemical and XPS investigations of cobalt in KOH solutions", J Appl. Electrochem., 30:1303-11 (2000).
Iwakura, et al., "The anodic evolution of oxygen on Co3O4 film electrodes in alkaline solutions", Electrochim Acta, 26:1319-26 (1981).
Jitaru, et al., "Electrochemical reduction of carbon dioxide on flat metallic cathodes", J Appl Electrochem., 27:875-89 (1997).
Kanan and Nocera, "In situ formation of an oxygen-evolving catalyst in neutral water containing phosphate and Co2+.", Science 321:1072-5 (2008).
Kanan, et al., "Structure and valency of a cobalt-phosphate water oxidation catalyst determined by in situ X-ray spectroscopy", J Am Chem Soc., 132:13692-710 (2010).
King, et al., "Kinetics of Nucleation, Growth and Stabilization of Cobalt Oxide Nanoclusters", J Phys Chem B., 107:12097-104 (2003).
Lewis and Nocera, "Powering the planet: chemical challenges in solar energy utilization", PNAS, 103:15729-35 (2006).
Lutterman, et al., "A self-healing oxygen-evolving catalyst", J Am Chem Soc., 131:3838-9 (2009).
Merrill and Dougherty, "Metal Oxide Catalysts for the Evolution of O2 from H20", J Phys Chem C, 112:3655-66 (2008).
Meyer, "Chemical approaches to artificial photosynthesis", Acc Chem Res., 22:163-70 (1989).
Miles, et al., "The Oxygen Electrode Reaction in Alkaline Solutions on Oxide Electrodes Prepared by the Thermal Decomposition Method", J Electrochem Soc., 125:1931-4 (1978).
Nocera, "The artificial leaf", Acc Chem Res, 45:767-76 (2012).
Pintado, et al., "Fast and persistent electrocatalytic water oxidation by Co-Fe Prussian blue coordination polymers", J Am Chem Soc., 135:13270-3 (2013).
Seley, et al., "Combinatorial search for improved metal oxide oxygen evolution electrocatalysts in acidic electrolytes", ACS Comb Sci, 15:82-9 (2013).
Smith, et al., "Photochemical route for accessing amorphous metal oxide materials for water oxidation catalysis", Science, 340:60-3 (2013).
Surendranath, et al., "Electrolyte-dependent electrosynthesis and activity of cobalt-based water oxidation catalysts", J Am Chem Soc., 131:2615-20 (2009).
Surendranath, et al., "Nucleation, growth, and repair of a cobalt-based oxygen evolving catalyst", J Am Chem Soc., 134:6326-36 (2012).
Tang, et al., "Characterization of Cobalt Oxides Studied by FT-IR, Raman, TPR and TG-MS", Thermochin Acta, 473:68-73 (2008).
Thomsen, et al., "Electrochemical activation of Cp* iridium complexes for electrode-driven water-oxidation catalysis", J Am Chem Soc., 136:13826-34 (2014).
Yagi, et al., "Self-assembly of active IrO2 colloid catalyst on an ITO electrode for efficient electrochemical water oxidation", J Phys Chem B., 109:21489-91 (2005).
Zaharieva, et al., "Electrosynthesis, functional, and structural characterization of a water-oxidizing manganese oxide", Energy Environ Sci., 5:7081-9 (2012).
Zhang and Ren, "Silica supported ruthenium oxide nanoparticulates as efficient catalysts for water oxidation", Chem Commun., 48:11005 (2012).

IRIDIUM COMPLEXES FOR ELECTROCATALYSIS

CROSS-REFERENCE TO RELATED APPLICATIONS

This application claims the benefit of and priority to U.S. Ser. No. 61/840,201 filed Jun. 27, 2013 and which is incorporated by reference in its entirety.

STATEMENT REGARDING FEDERALLY SPONSORED RESEARCH OR DEVELOPMENT

This invention was made with government support under 1119826 and 1122492 awarded by National Science Foundation and under DE-FG02-07ER15909 awarded by Department of Energy and under GM008283 awarded by National Institutes of Health. The government has certain rights in the invention.

FIELD OF THE INVENTION

This invention is in the field of iridium complexes for catalysis and corrosion protection. Catalytic processes include water-oxidation, C—H oxidation, halide oxidation, and oxygen reduction.

BACKGROUND OF THE INVENTION

Producing renewable clean energy is one of the most profound challenges of the 21$^{st}$ century. Most of the world's current energy supplies come from sunlight converted to chemical energy by photosynthesis in plants. Photosynthesis begins with light striking a light harvesting complex in Photosystem II, creating a charge-separated excited state where an electron is promoted to a higher energy level. Water oxidation catalyzed by an oxygen evolving complex (OEC) replenishes the hole derived from the charge-separated excited state. This process causes the release of four equivalents of $H^+$ per water molecule. Some of the generated protons are used in a proton gradient, which the plant employs to store energy by synthesizing ATP. The high energy electrons move along an electron transport chain and are eventually used to reduce the remaining protons from the water oxidation process.

A central thrust of current energy research focuses on artificial photosynthesis, namely synthetic light-harvesting, water-based fuel producing systems. Despite the intense global efforts to develop viable biological water splitting systems for energy production, breakthroughs are needed in efficiency and stability of the three operational units in such a composite system: the sensitizer for light absorption (charge separation), the catalyst for the proton-reduction half-reaction ($2H^+ + 2e^- \rightarrow H_2$), and the catalyst for the water-oxidation half-reaction ($H_2O \rightarrow O_2 + 4H+ + 4e-$).

Developing efficient and robust synthetic water-oxidation catalysts (WOCs) has proven particularly challenging, because this half-reaction is the most thermodynamically demanding part of water splitting. An effective WOC must be capable of water-oxidation at a potential minimally above the thermodynamic value (1.23 V at pH 0) to minimize energy losses. Furthermore, it should do this as quickly as possible to maximize space-time-yields of the overall device and to avoid charge accumulation (leading to corrosion) and recombination (energy loss). Finally, it has to be as robust as possible with regards to trace contamination, pH variations, current densities, and long-term operation to enable real-world application.

Both heterogeneous and homogeneous WOCs have been investigated. Heterogeneous WOCs consisting of bulk metal oxides, metal oxide layers or nanoparticles on conducting substrates generally have the advantages of ease of interface with electrode systems and good oxidative stability, but their synthesis is often laborious and leads to ill-defined materials that are hard to characterize and thus optimize. Furthermore, since only the surface layer of the electrode material is able to engage in the water-oxidation reaction at the interface with the aqueous solution their efficiency is inherently limited.

Homogeneous WOCs can be more amenable to spectroscopic, crystallographic, physiochemical, and computational investigation, and thus may be more readily optimized on a rational basis. Additionally, as each individual molecule of a homogeneous catalyst is capable of doing solution chemistry the efficiency of the process is intrinsically higher, thereby reducing the amount of catalyst needed. However, most of the known homogeneous WOCs that have been investigated are thermodynamically unstable with respect to oxidative degradation. As a result, no system has yet succeeded to combine the high efficiency of homogeneous WOCs with the durability and ease of application of heterogeneous ones. Such a catalyst system could be active in the reverse oxygen reduction reaction and electrode-driven hydrocarbon oxidations, the two key reactions of carbon fuel cells An alternative strategy to supply society with sustainable fuels, which circumvents the $H_2$ storage issues that are still problematic for a solar hydrogen economy, is the use of simple liquid hydrocarbons such as short chain alcohols, ethers, and lactones as energy carriers. As both biogenic and synthetic substrates could be used in such a scheme, a 'methanol economy' would serve as a flexible technology facilitating the transition to more sustainable energy supply. One of the key issues with this technology is, however, the energy-out part, i.e. the controlled total oxidation of the organic energy carrier in a low-temperature fuel cell. In a fuel cell, both the anode reaction (substrate oxidation to release protons & electrons) and the cathode reaction ($O_2$ reduction to $H_2O$) need effective electro-catalysts to maximize overall efficiency as explained above for the reverse case of water splitting.

Electrochemical total hydrocarbon oxidation to $CO_2$ at low temperatures is particularly challenging, and molecularly defined catalysts for this reaction are extremely rare. Preliminary evidence suggests that the catalysts also perform electrochemical hydrocarbon oxidation, which make them interesting for low-temperature direct carbon fuel cell applications. Furthermore, preliminary evidence suggest that the materials also catalyze the reverse reaction, electrochemical oxygen reduction, which is the ubiquitous cathode reaction in any type of fuel cell (including hydrogen fuel cells).

There exists a need for water oxidation catalysts that can split water at near-thermodynamic or extremely low overpotentials with a high turnover frequency for long periods of time without degrading, particularly using low cost materials or small amounts of highly active materials.

There exists a need for C—H oxidation catalysts that can selectively oxidize C—H bonds using an applied potential. A heterogeneous or surface bound molecular system is advantageous here because the reactants, products, and catalyst need to be separated at a later point, so having a catalyst that doesn't need to be separated is beneficial.

There is also a need for oxygen reduction reaction (ORR) catalysts that catalyze oxygen reduction at fuel cell cathodes, particularly at as low an overpotential as possible. Efficient ORR catalysts would dramatically increase the efficiency of fuel cells.

Therefore, it is an object of the invention to provide water oxidation catalysts that can split water at near-thermodynamic or extremely low overpotentials with a high turnover frequency for long periods of time without degrading, particularly using low cost materials or small amounts of materials and methods of making and using thereof.

It is also an object of the invention to provide C—H oxidation catalysts that can selectively oxidize C—H bonds using an applied potential, particularly heterogeneous or surface bound molecular catalysts which allow for straight forward separation of the reactants, products, and catalyst, and methods of making and using thereof.

It is also an object of the invention to provide catalysts for other electrochemical oxidation reactions, such as the oxidation of chloride to chlorine, bromide to bromine, and ammonia to nitric acid, particularly when using a surface bound molecular catalyst that allows for a lower overall energy cost in production of the product chemical.

It is also an object of the invention to provide oxygen reduction reaction (ORR) catalysts that catalyze oxygen reduction at fuel cell cathodes, particularly at as low an overpotential as possible and methods of making and using thereof.

SUMMARY OF THE INVENTION

Solution-phase (e.g., homogeneous) or surface-immobilized (e.g., heterogeneous) electrocatalysts based on iridium coordination compounds which self-assemble upon chemical oxidation of suitable precursors and methods of making and using thereof are.

Iridium species such as $\{[Ir(LX)_x(H_2O)_y(\mu-O)]_z^{m+}\}_n$ wherein x, y, m are integers independently selected from 0, 1, 2, 3, and 4, z and n are integers independently selected from 1, 2, 3, and 4, z and n from 1-4 and LX is an oxidation-resistant chelate ligand or ligands, such as such as 2(2-pyridyl)-2-propanolate, form upon oxidation of various molecular iridium complexes, for instance [Cp*Ir(LX)OH] or [(cod)Ir(LX)] (Cp*=pentamethylcyclopentadienyl, cod=cis-cis,1,5-cyclooctadiene) when exposed to oxidative conditions, such as sodium periodate ($NaIO_4$) or ceric ammonium nitrate (($NH_4$)$_2$Ce($NO_3$)$_6$, CAN) in aqueous solution at ambient conditions. During the course of this reaction the solution changes from a dull orange or yellow color to a characteristic deep blue, indicating formation of the active catalyst which has distinctively higher activity in electrocatalysis than the precursors. It is also more active than $IrO_x$ nanoparticles or films commonly obtained via similar procedures using other iridium precursors such as $IrCl_3$, [(cod)IrCl]$_2$, [Cp*IrCl$_2$]$_2$, or [Cp*Ir(H$_2$O)$_3$]SO$_4$.

The molecular blue iridium compound in solution has been found to be a very competent homogeneous electrocatalyst for water-oxidation. After formation, with no further modification, electrolysis of the aqueous solution at a gold electrode held at 1.6 V vs. NHE results in high sustained current concomitant with oxygen production as measured by Clark electrode. The oxygen yield is nearly quantitative; indicating that at this potential the catalyst operates with close to 100% Faradaic efficiency. No measurable water-oxidation activity is observed when subjecting the non-preoxidized precursors to the same conditions.

It was also found that the blue species generated in aqueous solution readily binds to various materials by simple immersion under ambient conditions. Not only does it bind very strongly, it retains its activity in electrocatalytic water oxidation on the surface of conducting oxide and other materials, as well as shows greatly improved stability when attached to surfaces.

If a catalyst proves stable under the conditions required for the reverse reaction, it must also catalyze it owing to the principle of microscopic reversibility, and this was found to be the case for the described molecular water-oxidation catalyst bound to the surface of an electrode. The oxygen reduction reaction is industrially relevant for fuel cells that are used to extract the chemical energy in molecular C—H, C—C, and H—H bonds. The catalysts have shown such activity under benign conditions that may pave the way for higher efficiency fuel cells, specifically that operate at low temperature. The homogeneous and heterogeneous catalysts exhibit extremely low overpotentials compared to the prior art at the point of catalysis for a specific current flow. For example, surface-bound heterogeneous catalysts show sustained current flow that increases linearly beginning at overpotentials of 15-20 mV for water oxidation, which corresponds to $E_{cat}$=1.25 V vs RHE, which is over an order of magnitude lower than the prior art. The energy required for catalysis ($E_{cat}$) using the catalysts is 110 mV lower than the prior art catalysts.

BRIEF DESCRIPTION OF THE DRAWINGS

FIG. 17e inset is a photograph of the electrode under turnover conditions (1.4 V vs. NHE, pH 2.6) corresponding to the Ir$^V$→Ir$^{III}$+O$_2$ spectrum.

DETAILED DESCRIPTION OF THE INVENTION

I. Definitions

Figure 1A:
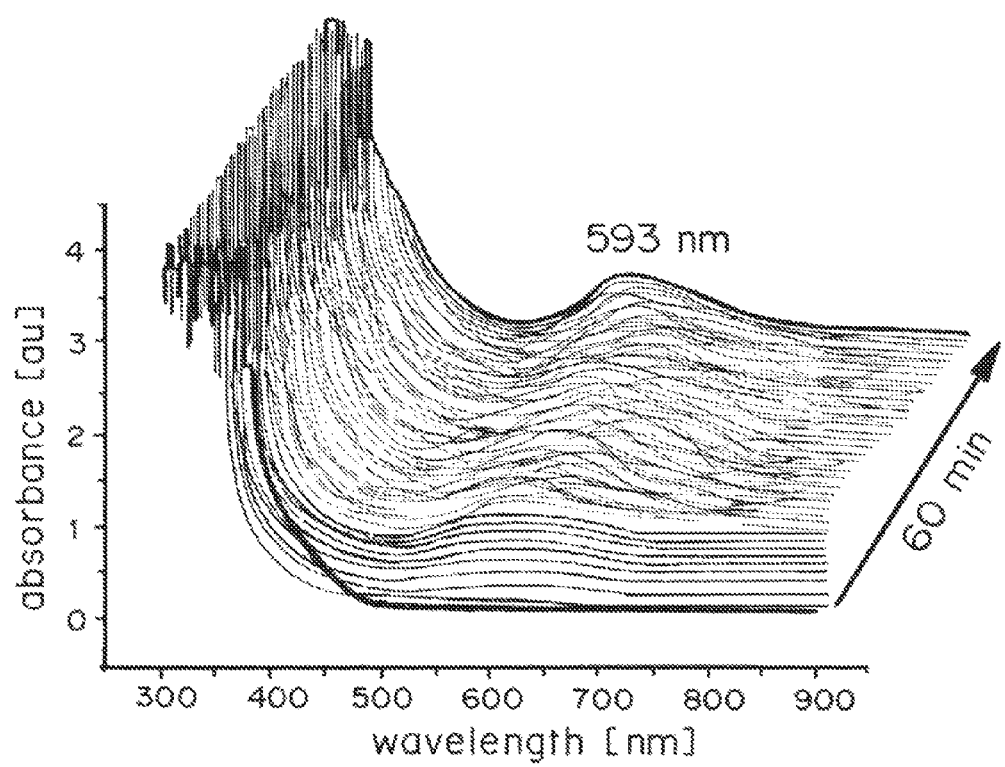
FIG. 1A is a full scan UV-Vis (absorbance [au] v. wavelength [nm]) time-course of the reaction shown in scheme 1 at 1 mM [Ir]+100 mM NaIO$_4$.

"Water oxidation catalyst", "WOC", "oxygen evolving catalyst", and "OEC" are used interchangeably and refer to a catalyst used to oxidize water to form oxygen (O$_2$) and hydrogen ions. Oxygen yield can be monitored using a variety of techniques. In one embodiment, oxygen yield is monitored using gas chromatography ("GC") by withdrawing gas samples from the reaction vessel headspace. In another, the solution concentration of oxygen dissolved in the aqueous reaction solution is quantified via an independent $O_2$ reduction electrode ("Clark electrode").

"Heterogeneous", as used herein, refers to the form of catalysis where the phase of the catalyst differs from that of the reactants "Homogeneous", as used herein, means the catalyst is soluble (i.e., same phase as the reactants) in the reaction solution.

"Molecular catalyst", as used herein, refers to catalysts that possess a defined, finite atomic structure, typically aggregates containing less than 4 molecular units of one metal center each (e.g., tetramers). In some embodiments, the aggregates are dimers.

"Oxidation-resistant ligand", as used herein, means that the ligand retains its molecular integrity throughout the oxidative activation step as opposed to the sacrificial place-holder ligands and remains at least partly bound to the metal center in the activated species thereby preventing polymerization to heterogeneous $IrO_x$ material. Examples of such include organic molecules based on, for example, pyridines, alkoxides, carboxylates, amides or carbenes that bind to the iridium in mono-, bi-, or tridentate fashions.

As used herein, "place-holder ligand" refers to a ligand which, when bound to an iridium atom, is susceptible to oxidative removal. Typically, placeholder ligands are bound to the metal through π-systems (e.g., olefinic and acetylenic bonds, or aromatic systems) only.

"Oxidatively stable" as used herein, means that more than 90%, more than 92%, more than 94%, more than 95%, more than 98%, more than 99%, more than 99.5%, more than 99.9%, more than 99.95%, more than 99.99% of the catalyst remain active or operational in the presence of one or more oxidants including, but not limited to, $O_2$, $O_3$, peroxides, and electrode-driven applied potentials, over a broad pH range (e.g., 0-11) for at least 7 days, 14 days, 21, days, 28 days, 30 days, 45 days, two months, three months, four months, five months, six months, one year, or longer at ambient temperature and ambient light conditions. Alternatively, the catalyst undergoes less than 10%, less than 5%, less than 1%, less than 0.5%, less than 0.1%, less than 0.05%, or less than 0.01% degradation under the conditions described above.

"Hydrolytically stable", as used herein, means that more than 90%, more than 92%, more than 94%, more than 95%, more than 98%, more than 99%, more than 99.5%, more than 99.9%, more than 99.95%, more than 99.99% of the catalyst molecules are structurally intact in the presence of water over a broad pH range (e.g., 3-9) for at least 7 days, 14 days, 21, days, 28 days, 30 days, 45 days, two months, three months, four months, five months, six months, one year, or longer at ambient temperature and ambient light conditions. Alternatively, the catalyst undergoes less than 10%, less than 5%, less than 1%, less than 0.5%, less than 0.1%, less than 0.05%, or less than 0.01% hydrolysis under the conditions described above. In a particular embodiment, the catalyst undergoes no structural changes under the conditions described above.

"Thermally stable", as used herein, means that more than 90%, more than 92%, more than 94%, more than 95%, more than 98%, more than 99%, more than 99.5%, more than 99.9%, more than 99.95%, more than 99.99% of the catalyst molecules are structurally intact at room temperature or lower or when heated to a temperature above room temperature. In a particular embodiment, the catalyst undergoes no structural changes when heated from room temperature to 60 C.

"Turn over number" or "TON", as used herein, means the number of moles of substrate that a mole of catalyst converts in the timeframe of the experiment or before being deactivated. TON is calculated as the number of moles of oxygen, $n_{O2}$, divided by the number of moles of iridium in the catalyst, $n_{cat}$.

"Turn over frequency" or "TOF", as used herein, refers to the turnover per unit time under turnover conditions. It is typically expressed in $s^{-1}$. The TOF can be calculated by dividing the TON by the time period, in seconds, over which the TON was measured.

"Turnover conditions", as used herein, refers to the conditions in which the catalytic reaction takes place. "Turnover conditions" typically include pH and temperature, concentration of the oxidant or the electrochemical potential applied, and concentration of the WOC. The turnover conditions and thus TONs and TOFs can vary for a given WOC.

"Oxygen yield", as used herein, refers to the percent oxygen formed during the catalytic reaction as compared to the maximum amount oxygen expected on the basis of oxidant added or current delivered.

"Oxidant" or "sacrificial electron acceptor", as used herein, refers to the molecule that is reduced during the oxidation of a substrate (e.g. water).

"Light collecting molecule" or "photo-sensitizer", as used herein, refers to the molecule in the catalytic system that absorbs light creating a charge separated excited state.

"Proton reduction catalyst" or "hydrogen evolving catalyst" are used interchangeably and refer to a catalyst that combines electrons and protons to form hydrogen gas.

II. Iridium-Based Catalysts

Molecular iridium-based homogenous and heterogeneous catalysts, particularly for water oxidation, C—H bond oxidation, and/or $O_2$ reduction, are prepared from catalyst precursors containing a sacrificial place-holder ligand, such as pentamethylcyclopentadienyl, $C_5Me_5^-$, and an oxidatively stable ligand. The place-holder ligand is removed from the metal during pre-activation to generate the active catalyst. The oxidatively stable ligand prevents aggregation/polymerization of the precursor to nanoparticles or other forms of heterogeneous metal oxide material. The active catalysts chemically bind to a variety of substrates that are useful for heterogeneous catalyst applications, such as water splitting or C—H bond splitting. The catalysts exhibit high turnover rates both in solution and bound to a substrate, and very high stability in the latter form. In solution, the catalysts exhibit almost quantitative oxygen conversion with Faradaic efficiencies of greater than 90, 91, 92, 93, 94, 95, 96, 97, 98, or 99%.

In one embodiment, the active catalyst is a compound of Formula (I):

$$\{[Ir^{IV}(LX)_x(H_2O)_y(\mu-O)]_z^{m+}\}_n \qquad (I)$$

wherein x, y, m are selected from 0, 1, 2, 3 and 4, and, z and n from 1, 2, 3 and 4, and LX is an oxidation-resistant ligand. In some embodiments, x is 1-2, y is 1-2, m is 1-2, z is 1-2 and n is 1-2. In other embodiments, x is 1, y is 2, m is 2, z is 1 or 2, and n is 1.

LX can be any ligand that is oxidatively stable. Suitable ligands include monodentate, bidentate, and tridentate ligands, and combinations thereof. Exemplary classes of ligands include, but are not limited to, N-heterocyclic carbenes (NHCs), pyridines, alkoxides, carboxylates, amides, phosphine oxides, and amino alkoxide. When used in the context of a ligand, "amino alkoxide" refers to a compound having nitrogen and oxygen atoms separated by 3 or 4 non-hydrogen atoms, wherein the nitrogen and oxygen atoms are capable of forming a ring with a metal atom.

In some embodiments, x and y and are as defined above and LX includes, but is not limited to, 2(2-pyridyl)-2-propanolate, 2,2'-bipyridine, 2-phenylpyridine, picolinate, and combinations thereof.

The catalyst can be prepared by oxidation of suitable precursor complexes in the presence of an oxidation-resistant chelate ligand. In one embodiment, the precursor is an organometallic iridium complex containing a placeholder ligand. The placeholder ligand is removed under oxidizing conditions in aqueous solution while the oxidation-resistant chelate ligand prevents oligomerization to form higher aggregates, such as nanoparticles or clusters of iridium oxide. In particular embodiments, the number of iridium atoms in the molecular catalyst is less than 4. In some embodiments, the number of iridium atoms is 2 (e.g. a dimer). Generally, the placeholder ligand is either weakly bound to the iridium or is susceptible to oxidative breakdown. Exemplary types of placeholder ligands include carbon monoxide, 1,5 cyclooctadiene (cod), cyclopentadienyl (Cp) and pentamethyl-cyclopentadienyl (Cp*) anions.

Suitable precatalysts include, but are not limited to, [Cp*Ir(bipy)OH]BF$_4$, [Cp*Ir(pyalc)OH], [(cod)Ir(bipy)]BF$_4$, [(cod)Ir(pyalc)] where bypy=2,2'-bipyridine and pyalc=2(2-pyridyl)-2-propanolate. Suitable placeholder ligands include, but are not limited to, pentamethylcyclopentadienyl (Cp*), cyclopentadienyl, phenylcyclopentadienyl, indenyl, (meth)allyl, 1,5-cyclooctadiene, 2,5-norbornadiene, cyclooctene, ethylene, and carbon monoxide.

In another embodiment, the catalyst is an iridium oxide (IrO) monolayer that is formed by heating an electrode coated with one or more of the precatalysts listed above to a temperature greater than about 500° C., or an iridium metal monolayer that is formed by heating the electrode to the same temperature in a reductive atmosphere, such as hydrogen gas. These monolayers can also be generated by exposing the precatalyst to electromagnetic radiation (e.g., laser, X-rays), chemicals (e.g., specific strong acids) in addition to or in place of heat.

A. Homogeneous Catalysts

The catalysts can be used as a homogeneous electrocatalyst. In solution, the catalysts exhibit turn over frequencies of from about 80 to about 200/minute, preferably about 70 to about 175/minute, more preferably about 85 to about 170/minute for water oxidation and from about 10-20 turnovers/minute, preferably from about 10 to about 15 turnovers/minute for C—H oxidation of ethylbenzene-sulfonate (EBS) to acetophenone-sulfonate (APS).

B. Heterogeneous Catalysts

The catalysts can also be used as heterogeneous electrocatalysts. The preformed homogeneous catalysts can be readily applied as monolayer on the surface of a solid substrate, such as the surface of an electrode. The monolayers can be cast from solution, and do not require an external stimulus (e.g., current (electrochemical)) for surface binding. The catalysts bind very strongly to a variety of substrates including, but not limited to, conductive substrates, photocatalytic substrates, and combinations thereof. Exemplary substrates include, but are not limited to, allotropes of carbon, such as carbon fiber, carbon wool, grapheme, nanotubes, etc., polymeric substrates (e.g., oxidatively resistant or conductive polymers), main group oxides such as tin-doped indium oxide (ITO), fluorine doped tin oxide (FTO), tin oxide (SnO$_2$), as well as transition metal oxides such as tungsten oxide (WO$_3$), iron oxide (Fe$_2$O$_3$), and titanium dioxide (TiO$_2$); carbon-based electrodes (typically used in fuel cells), such as glassy carbon, wooly carbon, and conductive carbon fiber; and metals, such as aluminum, copper, nickel, iron, lead, silver, titanium, and zinc. The substrate may also be a conductive polymers such as polyacetylenes, polyaromatics such as polyanilines, polyphenylenes, polypyrenes, polyazulenes and polynaphthalenes, polyheterocycles such as polypyrroles, polyanilines, polyindoles, and polyazepines, and olefin containing polymers such as poly(p-phenylene vinylene). The bonding is generally through covalent bonds, although in some instances the catalyst may be bonded to the substrate through ionic bonds. Many of these metals oxidize easily, so the catalyst may adhere to an oxide layer on the metal surface and not the metal itself "Strong binding" as used herein means that the bond remains substantially intact over a wide pH range (e.g., 0-11), in a variety of organic and inorganic solvents, and in water over time.

The heterogeneous catalysts exhibit significantly higher turnover numbers and turnover frequencies for water-oxidation and/or C—H oxidation compared to prior art catalyst systems. For example, surface-bound ruthenium based catalysts oxidize benzyl alcohol to benzaldehyde (85 kcal/mol BDE) at current corresponding to 2400 turnovers over 16 hours with 66% faradaic efficiency, which equates to a C—H oxidation TOF of about 1.6 turnovers per minute. In contrast, the surface-bound catalysts are capable of oxidizing more difficult substrates such as EBS (90 kcal/mol BDE) at a 7% conversion rate for 100 mg of EBS over 12 hours from 0.01 µm surface-bound catalyst. Under these non-optimized conditions, this corresponds to a TOF of about 5 turnovers per minute. In some embodiments, the catalysts exhibit a TOF for C—H oxidation of EBS of at least 2.0, 2.5, 3.0, 3.5, 4.0, 4.5, 5.0. 5.5, 6.0 or greater.

Prior art water-oxidation catalysts are generally not able to catalyze electrode-driven C—H oxidation. Single-site heterogeneous catalysts in the form of monolayers, exhibit much higher activity.

III. Methods of Making the Precatalysts/Catalysts

The precatalysts are synthesized starting with an iridium species bearing a placeholder ligand or ligands that are easily removed by oxidative activation, and mono-, bi-, or tri-dentate coordinating ligands with a much higher degree of oxidative stability. The catalysts are then formed by adding the precatalyst of Formula (II) to water and combining with equivalents of a chemical oxidant sufficient to remove the placeholder ligand or ligands, or applying an electrochemical potential in a bulk electrolysis scheme sufficient to remove the placeholder ligand.

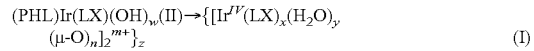

(PHL)Ir(LX)(OH)$_w$(II)→{[Ir$^{IV}$(LX)$_x$(H$_2$O)$_y$(µ-O)$_n$]$_2^{m+}$}$_z$     (I)

wherein LX, x, y, n, m, and z are as defined above, PHL is a placeholder ligand, and w is selected from 0-3.

In a typical case, the pentamethylcyclopentadienyl ligand acting as a placeholder requires at least 20 equivalents of a chemical oxidant, or an electrochemical potential of at least 1.4 V vs. NHE. Upon treatment with an electrochemical or chemical oxidant, the iridium in the precatalyst oxidizes to Ir(IV), typically but not always displaying a dark blue color. In some embodiments, the oxidation state changes from Ir(IV) to Ir(III), or Ir(V) during or after formation of the resting state catalyst in water at room temperature.

The general deposition/heterogenization procedure for the catalysts involves immersion of the substrate material into the aqueous solution containing the catalyst for a period of time, typically around two hours. The catalyst then automatically binds to the surface by water elimination. The full preparation of the heterogeneous catalyst, starting from an organometallic precatalyst, can be seen with one specific example, a catalyst bearing a 2(2-pyridyl)-2-propanolate on a metal oxide surface, in the scheme below.

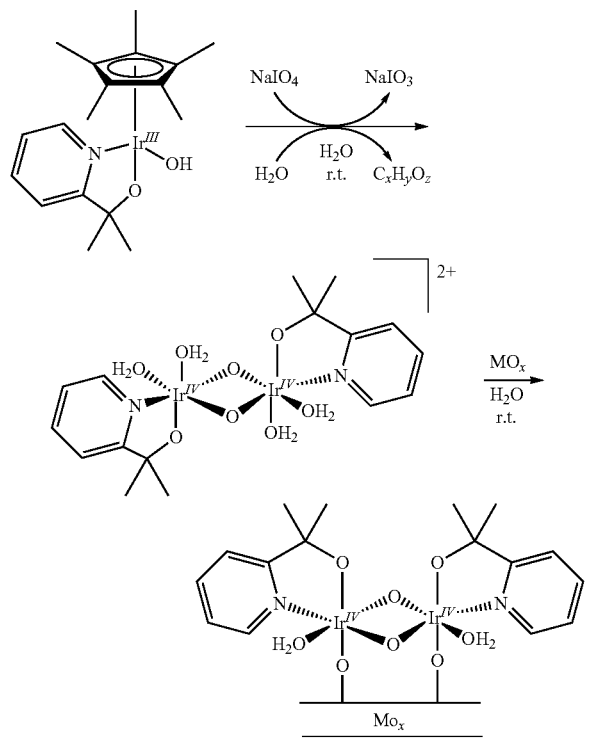

IV. Methods of Use

A. Water Oxidation

The catalysts can be used in a variety of devices. In one embodiment, the device is a cell containing an anode and a cathode. The cathode can also be used to drive a variety of reduction reactions, such as metal deposition or refining, electroplating, galvanization, dihydrogen production, $CO_2$ reduction etc.

In some embodiments, water is oxidized to oxygen at the anode in the presence of the WOC and hydrogen gas is evolved at the cathode. In some embodiments, the cathode contains a hydrogen evolution catalyst, for example, coated on the cathode surface. Suitable hydrogen evolution catalysts include, but are not limited to, tungsten disulfide, molybdenum disulfide, cobalt tetraimines, cyclopentadienyl ruthenium-nickel catalysts, samarium hydroxide, colloidal platinum catalysts stabilized by polyvinyl alcohol, dinuclear iron complexes, which are efficient catalysts for hydrogen evolution, macrocyclic cobalt and nickel complexes, noble metals, and noble metal oxides and sulfides. Other hydrogen evolution catalysts are known in the art.

The anode and cathode can be made from materials known in the art. Such cells are known in the art and can be designed to conduct the reaction on any scale, including industrial scale. Alternatively, the reaction can be conducted in a cell irradiated with light to drive the anodic water oxidation and cathodic reduction reaction (of any kind described above)

In still another embodiment, the reaction can be take place in the presence of a supramolecular system, such as a nanomaterial or nanostructure. Such systems can be used to imitate photosynthesis by conducting both water oxidation and proton reduction in the same molecular system. For example, in one embodiment, water is oxidized in the presence of a WOC, at one end or part of a nanomaterial or nanostructure to produce oxygen, hydrogen ions, and electrons. The electrons are transported rapidly to another part of the nanomaterial or nanostructure, where a water reduction catalyst (hydrogen evolution catalyst) catalyzes the reduction of hydrogen ions by electrons to form hydrogen gas.

Supramolecular systems include molecular assemblies and composite materials. Exemplary materials include inorganic materials, such as high performance semiconducting nanomaterials and hierarchically assembled nanostructures. The materials can be designed to enhance light absorption, for example, by the incorporation of molecular antennae. Inorganic-organic hybrid materials with enhanced light absorption and tunable bandgaps can be used as platforms for the catalysts. Other materials include nanotubes, nanosheets, etc., such as those prepared from $TiO_2$, other inorganic materials, and organic materials. Molecular assemblies can be prepared from polymers and polypeptides. Exemplary structures include polymer and coiled-coil polypeptide assemblies that can precisely position molecular subunits in three dimensions. Light harvesting assemblies prepared from polymers, such as one-dimensional polymers, that absorb sunlight and efficiently transport the excited state energy over long distances can also be used. Finally, printing technology can be used to design, fabricate, and test nanostructured metal-oxide electrodes for improved light capture in solar fuel devices.

The hydrogen gas produced in the device described above can be separated from the oxygen gas. The hydrogen gas can be captured and stored until use. Alternatively, the devices described above can be linked to a hydrogen fuel cell or combustion reactor so that the hydrogen gas is fed directly into the end device. The product of hydrogen combustion/hydrogen consumption is water. This water can be recycled and reoxidized using the catalysts and methods of use. Oxygen is also produced in the catalytic reaction. Oxygen can be captured and stored and used for a variety of applications which oxygen production is desirable. Alternatively, it can be released to the atmosphere to be available for fuel cells in other places through natural cycles.

The catalysts can be incorporated into one or more of the devices discussed above or other devices suitable for water-oxidation and the devices sold to the end user. Alternatively, the catalysts can be provided in a kit. The kits contains the catalyst in a container, along with instructions for use of the catalyst, and the end user incorporates the catalyst into one of the devices discussed above or another device useful for water oxidation. For industrial scale processes, the amount of catalyst to be used can vary from grams to kilograms to pounds. One of ordinary skill can readily determine the amount of catalyst need for a particular application on a particular scale.

1. Electrochemical Fuel Cells

A fuel cell is generally an electrochemical cell that converts a reduced source fuel and oxygen into an electrical current and the oxidized form of the fuel (water in case of hydrogen fuel cells, $CO_2$ and water in case of methanol fuel cells, etc.). It generates electricity inside a cell through reactions between a fuel and an oxidant, triggered in the presence of an electrolyte. The reactants flow into the cell, and the reaction products flow out of it, while the electrolyte remains within it. Fuel cells can operate virtually continuously as long as the necessary flows are maintained.

Fuel cells are different from conventional electrochemical cell batteries in that they consume reactant from an external source, which must be replenished, a system known as a thermodynamically open system. A hydrogen fuel cell uses hydrogen as its fuel and oxygen (usually from air) as its oxidant. Other oxidants, such as chlorine or chlorine dioxide can also be used. Examples of hydrogen fuel cells include, but are not limited to, proton exchange fuel cells, solid oxide fuel cells, and molten carbonate fuel cells.

Applications of hydrogen fuel cells include power sources for automobiles and other vehicles, such as industrial equipment and power sources for remote locations, such as remote weather stations, large parks, rural locations, and in certain military applications. Hydrogen fuel cells can also be used to power small electronic devices where AC charging may not be available for weeks at a time, such as notebook computers, portable charging docks for small electronics (e.g. a belt clip that charges your cell phone or PDA), smartphones, GPS units, and small heating appliances. A fuel cell system running on hydrogen can be compact and lightweight, and have no major moving parts. Because fuel cells have no moving parts and do not involve combustion, they have high reliability, resulting in minimum down time and long lifetime.

2. Hydrogen Combustion

Hydrogen can be combusted in the presence of air to produce energy. For example, hydrogen fuel, purified oxygen, and water can be fed into a combustor. The only product of the reaction is steam, since there are no contaminants in the oxygen which can produce pollutants, such as $NO_x$. The resulting steam can be used to power a gas turbine. Beyond combustion, $H_2$ is the largest chemical feedstock produced by mankind and essential for countless processes, including the Haber-Bosch to produce ammonia for fertilizer that feeds most of the world, but it is currently produced almost exclusively from fossil fuel-based feedstocks. Therefore as fossil fuels diminish, sustainable $H_2$ production will become extremely important for the future chemical industry.

Alternatively, a process known as chemical looping can be used for hydrogen combustion. Chemical looping uses two successive reactions: metal oxide reduction with hydrogen and subsequent oxidation of the metal with pressurized air to yield the metal oxide and a high temperature flue gas. The resulting flue gases can be used to power turbines. Pure hydrogen is an ideal fuel for chemical looping and because there is no flame that can produce $NO_x$, purified oxygen is not required.

B. Carbon-Hydrogen Bond Oxidation

The catalysts detailed herein can be used for the synthesis of commodity and specialty chemicals that are made by selective oxidation of precursor organic species possessing C—H bonds. This can be as a single step of a multi-step synthesis to form a complex product, as a stand-alone catalytic reaction to transform one chemical into another single chemical or group of chemical products, or to oxidatively degrade harmful or unwanted organic compounds to less harmful, highly oxidized, compounds such as acetate, formate, carbonate, and/or carbon dioxide. Oxidants that can be used with this catalyst include, but are not limited to, electrochemical oxidants (an applied electric potential), chemical oxidants including, but not limited to, Oxone, potassium hydrogen peroxysulfate ($KHSO_5$), hydrogen peroxide, oxygen, ozone, or a combination of chemical and electrochemical oxidants.

Applications of carbon-hydrogen bond oxidation using this catalyst include bulk commodity chemical synthesis, remediation of organic waste, and synthesis of specialty chemicals due to selective oxidation of specific carbon-hydrogen bonds in an organic species.

In addition to waste treatment, carbon-hydrogen bond oxidations are of particular interest because controlled electro-oxidations of liquid fuels, such as methanol to $CO_2$, are highly desirable for low-temperature fuel cell applications. Also, selective partial functionalization of hydrocarbons is useful for the upgrading of unreactive feedstocks. For example, tetrahydrofuran (THF) oxidation at 1.2 V vs. NHE and heterogeneous oxidation of ethylbenzene-sulfonate (EBS) to acetophenone-sulfonate (APS).

C. Metal Deposition/Electroplating/Metal Refining

In other embodiments, water is oxidized at the anode, and metal ions are reduced to metals ($Zn^{2+} \rightarrow Zn$ or $Cu^+ \rightarrow Cu$ etc.) at the cathode. In some embodiments the metal is deposited as a coating on the cathode (electroplating, electrogalvanization), and in other embodiments the metal is deposited on the cathode as crystals, powder, foam or nodules, which may be removed from the cathode.

D. Monolayers

As described above, the catalysts can be used to deposit an IrO monolayer or nanoparticles less than 50 nm by treatment with heat (e.g, 500-700° C., a source of electromagnetic radiation (e.g., laser, X-rays), or chemical treatment. The monolayers can be used to coat a substrate to prevent substrate corrosion and/or to tune one or more properties of the substrate, such as hydrophobicity or surface conductivity/resistivity. Alternatively, treatment with heat and a reductant such as $H_2$ can be used to fabricate films or nanoparticles of metallic Ir on surfaces for heterogeneous catalytic applications such as selective hydrogenations, de-$NO_x$-ification, isomerizations, and alkane reforming.

E. Oxidation of Halides

The catalysts can be used for the electrochemical oxidation of halide ions in solution to form their complementary halogen compounds. This includes, but is not limited to, the electrochemical generation of $Cl_2$ from $Cl^-$ in aqueous solution and the electrochemical generation of $Br_2$ liquid from $Br^-$ in aqueous solution. These reactions are used in large-scale industrial systems that use electrochemical oxidation as a single-step or an intermediate step in the synthesis of commodity or specialty chemicals.

EXAMPLES

Reagents

Organic solvents were purified by passing over activated alumina with dry $N_2$. 18 MΩcm water was supplied by a Millipore purification system. All chemicals were purchased from major commercial suppliers and used as received. Syntheses were performed under an inert atmosphere of dry $N_2$ using standard Schlenk techniques.

Pre-Catalyst and Catalyst Synthesis

[(η5-pentamethylcyclopentadienyl)$Ir^{III}(H_2O)_3$]$SO_4$, [(η5-pentamethylcyclopentadienyl)$Ir^{III}$(2,2'-bipyridine-κN, κN')OH]$BF_4$ (1) and [(η5-pentamethylcyclopentadienyl)$Ir^{III}$ (2-(2'pyridyl)-2-propanolate-κO,κN)OH] (3) were prepared using known methodologies.

[(η5-pentamethylcyclopentadienyl)$Ir^{III}$(1,3,5-triazacyclononane-κN,κN,κN)]$SO_4$ (2): Solid 1,3,5-triazacyclononane (16 mg, 0.12 mmol) was added to an aqueous solution of freshly prepared [Cp*Ir($H_2O$)$_3$]$SO_4$ (0.1 mmol in 5 mL). The yellow solution was stirred for 16 hours at room temperature and then taken to dryness under reduced pressure. The solid residue was taken up in 2 mL of dry methanol and the solution filtered through 0.2 μm pore size Teflon filter. Addition of 12 mL Et$_2$O caused precipitation of a fine solid, and after taking off the pale yellow supernatant a colorless powder remained which was dried in vacuo. Yield 43 mg (78%). $^1$H-NMR (400 MHz, D$_2$O): δ=3.09 (m, 6H), 2.95 (m, 6H), 1.81 (s, 15H). $^{13}$C-NMR (126 MHz, D$_2$O): δ=88.1, 52.2, 7.8.

[(η2-cis-cis-1,5-cyclooctadiene)Ir$^I$(2,2'-bipyridine-κN,κN')]BF$_4$ (4): This compound was prepared via an alternative route. [(cod)IrCl]$_2$ (67 mg, 0.1 mmol) and 2,2'-bipyridine (31 mg, 0.2 mmol) were combined in dry CH$_2$Cl$_2$ (5 mL), immediately yielding a dark purple solution. NaBF$_4$ (33 mg, 0.3 mmol) in H$_2$O (3 mL) was added, and the biphasic mixture stirred vigorously for one hour at room temperature. The colorless aqueous phase was removed, the dark brown organic phase washed with water (2×2 mL), and dried over MgSO$_4$. After filtration through 0.2 μm pore size Teflon filter Et$_2$O was added (10 mL), causing precipitation of a fine, dark orange solid which was collected and dried in vacuo. Yield=76 mg (70%). $^1$H-NMR (400 MHz, CD$_2$Cl$_2$): δ=8.46 (d, J=8.1 Hz, 2H), 8.33 (t, J=7.7 Hz, 2H), 8.13 (d, J=5.3 Hz, 2H), 7.75 (t, J=6.4 Hz, 2H), 4.41 (m, 4H), 2.44 (m, 4H), 2.05 (q, J=7.9 Hz, 4H). $^{13}$C-NMR (126 MHz, CD$_2$Cl$_2$): δ=158.6, 149.4, 142.9, 128.9, 124.7, 71.2, 31.8.

[(η$^2$-cis-cis-1,5-cyclooctadiene)Ir$^I$(2-(2'pyridyl)-2-propanolate-κO,κN)] (5): 2-(2'pyridyl)-2-propanol (28 mg, 0.2 mmol) was dissolved in dry THF (10 mL) and n-butyllithium in hexanes (125 μL of a 1.6 M solution, 0.2 mmol) was added drop wise at room temperature. The clear, colorless solution was then added to a solution of [(cod)IrCl]$_2$ (67 mg, 0.1 mmol) in dry THF (10 mL) via cannula, causing an gradual color change from orange to yellow. The solution was stirred for 10 minutes at room temperature and then taken to dryness under reduced pressure. Et$_2$O was added (10 mL) to the solid residue, the mixture briefly sonicated, and filtered through 0.2 μm pore size Teflon filter. Evaporation of solvent under reduced pressure and drying in vacuo yielded a yellow-orange powder. Yield=74 mg (85%). $^1$H-NMR (400 MHz, CD$_2$Cl$_2$): δ=7.92 (d, J=5.6 Hz, 1H), 7.80 (td, J=7.9 Hz, J=1.5 Hz, 1H), 7.43 (d, J=8.1 Hz, 1H), 7.20 (ddd, J=7.2 Hz, J=5.7 Hz, J=1.3 Hz, 1H), 4.15 (m, 2H), 3.11 (m, 2H), 2.24 (m, 4H), 1.68 (m, 4H), 1.48 (s, 6H). $^{13}$C-NMR (126 MHz, CD$_2$-Cl$_2$): δ=183.0, 146.9, 138.3, 123.1, 122.6, 86.9, 68.1, 52.8, 34.7, 32.7, 31.8. ESI(+) MS calcd for C$_{16}$H$_{21}$IrNO$^+$: 434.123, 436.126. Found: m/z=434.122, 436.125.

Instrumentation $^1$H and $^{13}$C-NMR spectra were recorded at room temperature on either 400 MHz or 500 MHz Bruker Avance spectrometers and referenced to residual protio-solvent signals (δ in ppm). $^{17}$O-NMR was performed on a 500 MHz Bruker Avance spectrometer equipped with a 5 mm ATMA broadband probe operating at 67.8 MHz controlled through TopSpin (version 1.3). Samples were prepared by dissolving the solid reagents in 10% $^{17}$OH$_2$ (Enritech Enrichment Technologies LTD) at least 15 min prior to the analysis. Measurements were performed with sample spinning but without lock and sweep using the following parameters: p1=10 μs, d1=100 ms, aq=100 ms, sw=1400 ppm, ns=150.000. Spectra were manually phased and baseline corrected with apodization to 20 Hz line broadening, and the free water line centered to 0 ppm. Paramagnetic susceptibility measurements by $^1$H-NMR were performed at room temperature on a 400 MHz Bruker Avance spectrometer.

UV-Vis spectra were recorded at 1 nm resolution on a Varian Cary 50 using 1.0 cm quartz cuvettes against a background of neat solvent. Kinetics were monitored with 0.2 Hz at the given wavelength.

MALDI-TOF-MS measurements were performed using an Applied Biosystems (AB)/MDS Sciex Model 4800 MALDI-TOF/TOF mass spectrometer with AB 4000 Series Explorer software (version 3.6). An aqueous solution of 0.1 mM 3 and 1 mM NaIO$_4$ was stirred for ~2 minutes at room temperature, after which a 1 μL aliquot was withdrawn and mixed with 99 μL matrix solution (16 mM α-cyano-4-hydroxycinnamic acid in 1:1 MeCN/H$_2$O). 1 μL portions of the quenched mixture were spotted onto the MALDI target plate, dried in air, introduced to the HV chamber, and ionized with a YAG laser at 355 nm (200 Hz). Spectra were acquired over the mass range 300-2000 m/z in reflector positive mode summing 2000 laser shots.

TEM images and EDX spectra were taken using a FEI Osiris 200 kV TEM. Samples were prepared by oxidizing a 5 mM aqueous solution of 3 with 200 mM NaIO$_4$ for one hour at room temperature, evaporation of solvent at 50° C., drying in high vacuum, and depositing the resulting bluish powder onto SiO or lacey carbon copper TEM grids (Ted Pella) as a suspension in dry CH$_2$Cl$_2$. Peak deconvolutions were performed using TIA software.

XPS spectroscopy was performed using aluminum Kα photons (hv=1486.6 eV) and a double-pass cylinder mirror analyzer (PHI 15-255G). Samples were prepared by pressing some of the solid sample prepared for TEM-EDX onto a 0.1 mm thick disc (1 cm diameter) of high purity gold (99.99%, Ted Pella) using a bench-top pellet press at 2000 psi. Spectra were referenced using gold as internal standard, and peak fits were performed using XPSPeak (version 4.1).

Raman spectra were collected on a Spex 1403 Ramalog Double Laser-Raman spectrometer interfaced with a Spex DM3000 data acquisition system (used in direct photon-counting mode) and based upon a Spectra-Physics Stabilite 2017 argon-ion laser or a Horiba Jobin-Yvon T64000 Raman spectrometer with triple subtractive monochromator and an Ignis 660 diode laser. Samples were prepared in spectral grade water at least 30 minutes prior to the analysis, and a background of pure water was collected before the sample was measured at room temperature (5 seconds integration time at 2 cm$^{-1}$ resolution [Spex] or 60 seconds integration time at 0.1 cm$^{-1}$ resolution [Horiba]). Raman-shift calibrations were performed by either scanning over the excitation line (Spex, with reduced slit width) or with a silicon reference sample (Horiba). Plasma lines from the argon-ion excitation source were manually removed from the 488 nm spectrum, which then was interpolated with a B-spline function.

O$_2$ assays were run at 25° C. using a temperature-controlled YSI Clark-type electrode setup with a Versastat 4 potentiostat from Princeton Applied Research. After zeroing with NaHSO$_3$ solution, the electrode was allowed to stabilize in 5 mL of a freshly prepared, air-saturated aqueous oxidant solution (10 mM NaIO$_4$) for 3-5 minutes with stirring before injecting 250 μL of a 0.1 mM catalyst solution to start the catalysis. Averages of 100.000 individual data points were collected with 6 Hz until saturation of the electrode (~250 μM O$_2$).

CH-oxidations were run by pre-dissolving 0.2 mmol of a substrate (42 mg EBS) and 2 mmol of an oxidant (428 mg NaIO$_4$) in 5 mL of water at room temperature, and then injecting 200 μL of a 10 mM catalyst solution to start the reaction. Conversions were determined from $^1$H-NMR using 40 mM sodium d$_4$-trimethylsilylpropionate as internal standard.

Example 1. Oxidative Transformation of Pre-Catalyst [Cp*Ir(bipy)OH]BF$_4$ (1)

[Cp*Ir(bipy)OH]BF$_4$ (1) was reacted with NaIO$_4$ in H$_2$O (scheme 1).

Scheme 1. Oxidation of yellow [Cp*Ir(bipy)OH]BF$_4$ to a blue species.

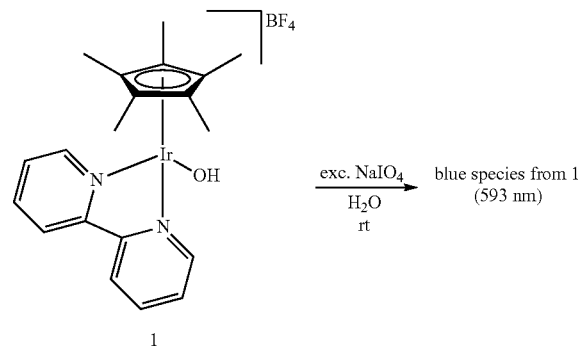

1

Figure 1B:
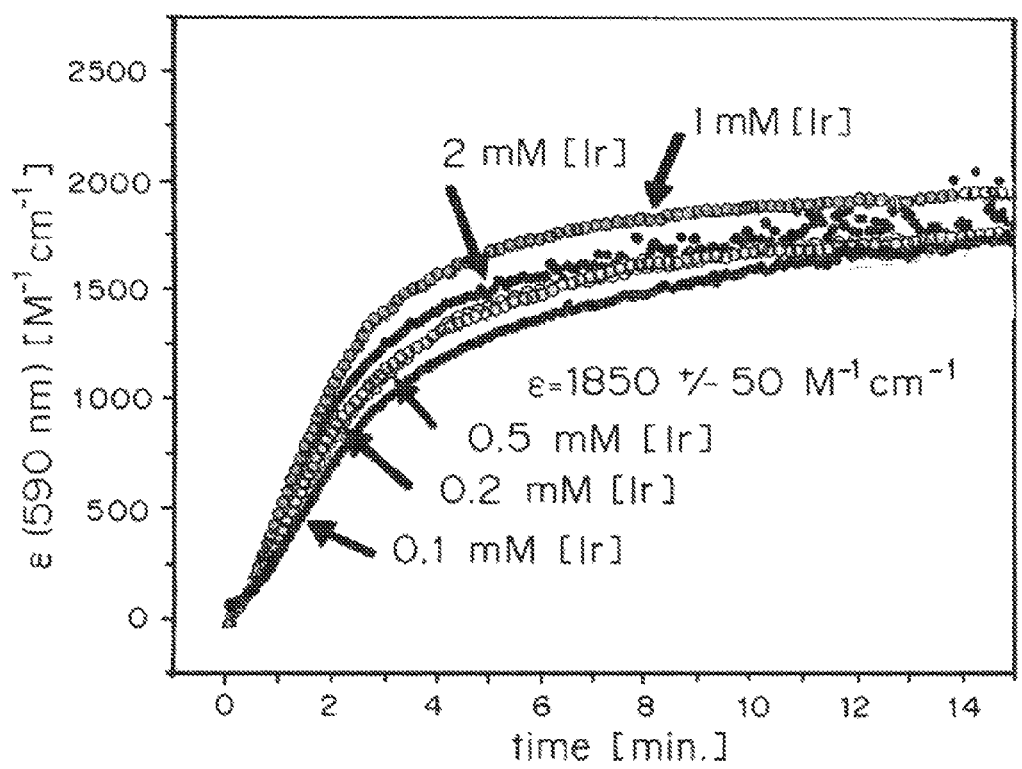
FIG. 1B is a kinetics plot [ε v. time (min)] of the 590 nm absorption band at 100 mM NaIO$_4$ showing the rate of precursor activation.

The reaction was monitored by UV-Vis spectroscopy. As shown in FIG. 1, a smooth evolution of the characteristic λmax~590 nm over the course of several minutes (FIG. 1A) was observed, making the reaction well suited for kinetic studies (FIG. 1B).

Figure 2A:
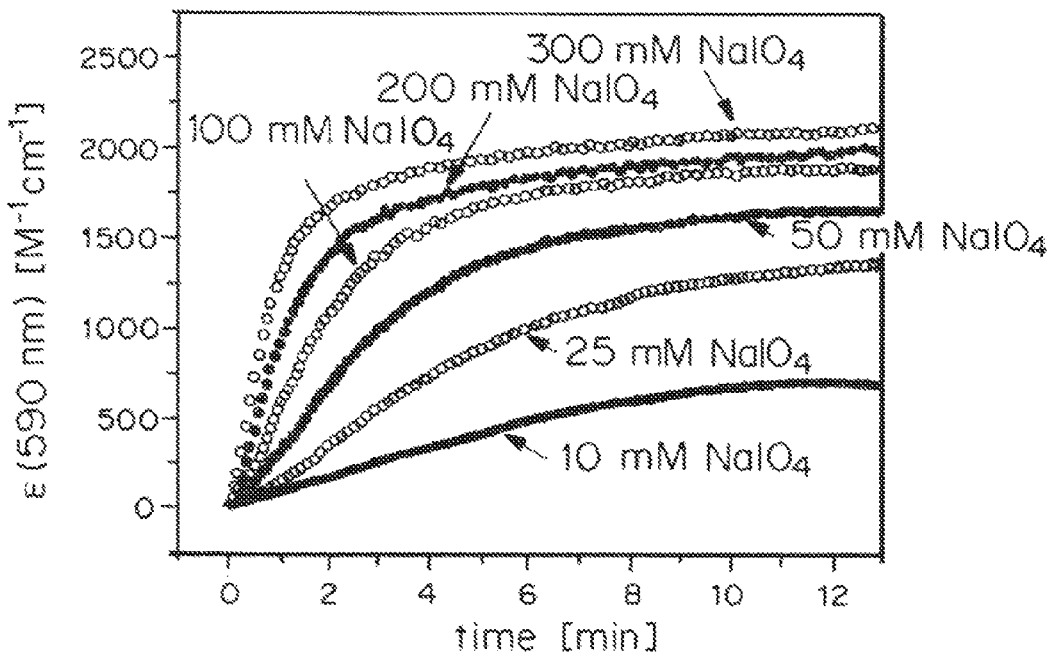
FIGS. 2A and 2B are UV-Vis kinetics plots [ε v. time (min)—FIG. 2A, ε v. NaIO$_4$ (mM)—FIG. 2B] of the reaction shown in scheme 1 at 1 mM [Ir] monitored at 590 nm.
Figure 2B:
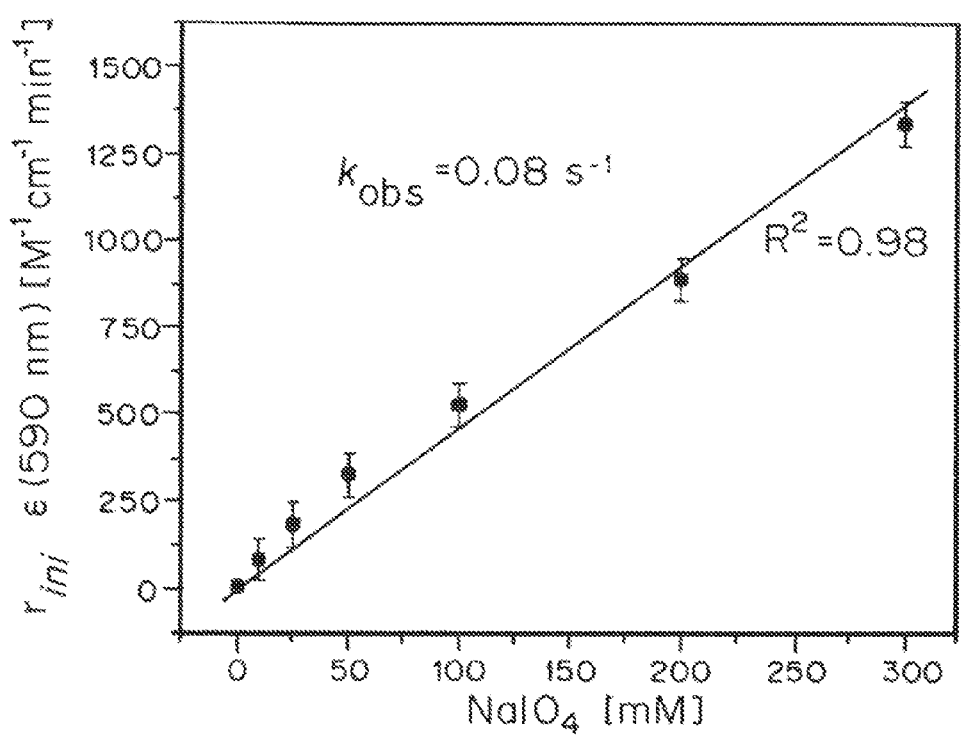

Variation of iridium concentration showed the rate of the reaction to be independent of [Ir] over more than one order of magnitude (FIG. 2), whereas variation of NaIO$_4$ concentration showed a first-order rate dependence on oxidant (FIG. 2). Thus, the rate-determining step of the formation of the blue species appears to be the initial oxidation of the Cp* precursor, which proceeds with an apparent first-order rate constant kobs=0.08 s-1 corresponding to a half-life time of about 9 seconds for 1 under these conditions. Furthermore, the electronic transition at ~590 nm likely involves a single metal center since identical final molar absorptivities of ε590≈1850 M-1 cm-1 were found over a wide range of iridium concentrations (FIG. 1B).

Figure 3A:
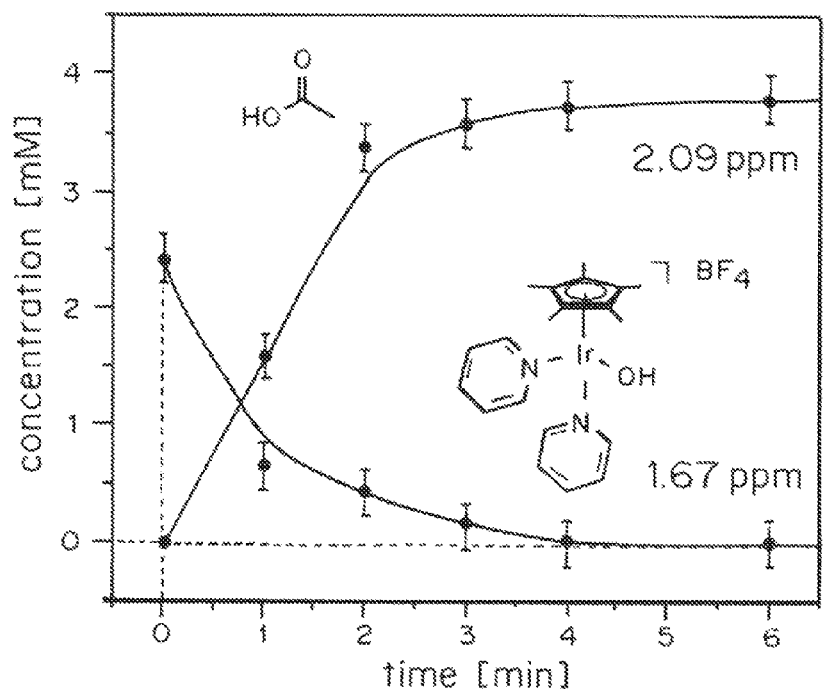
FIG. 3A is a $^1$H-NMR time-course of the reaction of 1 at 2 mM with 100 mM NaIO$_4$ in H$_2$O as measured from samples quenched with NaHSO$_3$+sodium d$_4$-trimethylsilylpropionate (20 mM) in D$_2$O [(concentration (mM) v. time (min)].
Figure 3B:
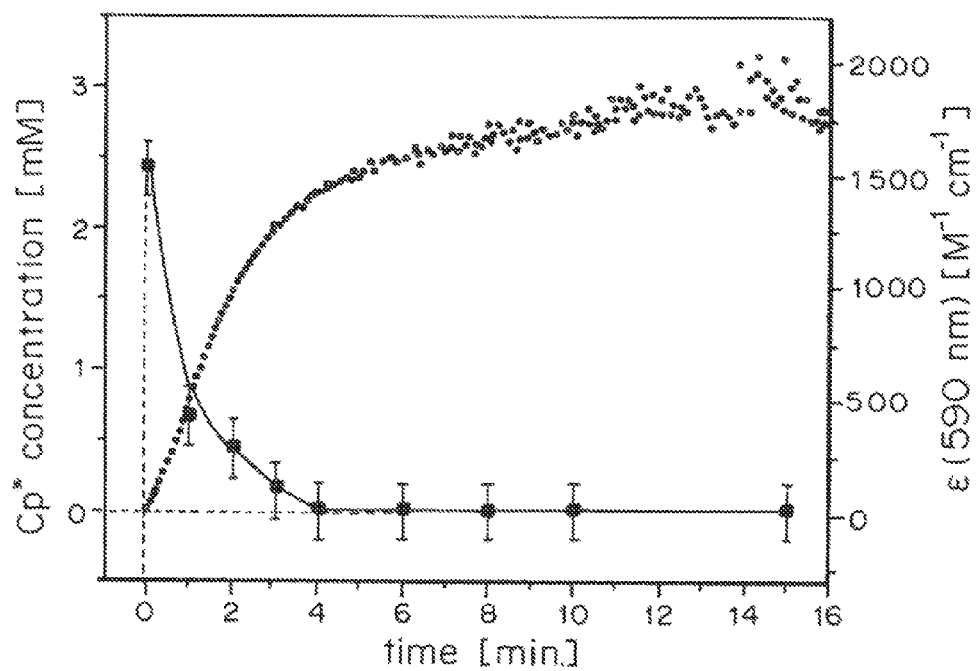
FIG. 3B is a comparison with UV-Vis kinetics of the same reaction monitored at 590 nm [Cp* concentration (mM) v. time (min)] illustrating oxidative Cp* removal to be concomitant with the formation of the active catalyst.

$^1$H-NMR analysis of sampled aliquots quenched with NaHSO$_3$ showed a progressive disappearance of the Cp* peak over time with build-up of acetic acid to a final level of ~1.8 equiv. per [Ir] (FIG. 3A). No signals from partially oxidized 1 or other organic fragments were detected by $^1$H- and $^{13}$C-NMR, but some split and broadened peaks of the bipy ligand remained visible in the aromatic region. Importantly, monitoring the reaction by UV-vis spectroscopy under the same conditions showed Cp* loss to be concomitant with build-up of the absorption at 590 nm (FIG. 3B), suggesting the blue species to be an oxidized form of 1 lacking the Cp* ligand.

Example 2. Mechanism of Cp* Removal and Formation of Active Catalytic Species In order to test how the Cp* ligand is oxidatively removed from the Ir$^{III}$ precursor, the coordinatively saturated sandwich complex [Cp*Ir(tacn)]SO$_4$ (2, tacn=1,3,5-triazacyclononane) was prepared and treated with excess NaIO$_4$ in H$_2$O (Scheme 2).

Scheme 2. Inertness of [Cp*Ir(tacn)]SO$_4$ toward oxidation with aqueous NaIO$_4$.

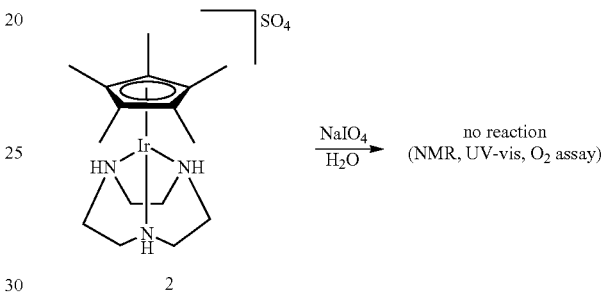

2

In this case, the $^1$H-NMR and UV-Vis spectra of the complex remained entirely unchanged, and no O$_2$ evolution was detectable by Clark-type electrode. The complete inertness of 2 towards oxidation demonstrates that neither direct oxidant attack on the coordinated Cp* ligand or outer-sphere electron transfer from the Ir$^{III}$ to the oxidant appears to occur, and oxidative transformation of Cp*Ir$^{III}$ complexes thus occurs within the coordination sphere of the metal, requiring at least one open site to proceed.

While [Cp*Ir(bipy)X]$^+$ complexes with various hydrolysable X ligands in the open site readily react with aqueous periodate, no reaction occurred between [Cp*Ir(bipy)Cl]BF$_4$ and [NBu$_4$][IO$_4$] in dry CH$_2$Cl$_2$ (Scheme 3). Thus, in addition to an open site, water is also needed for oxidative activation of the Cp*Ir precursor with NaIO$_4$, either by providing an Ir—OH$_{(2)}$ moiety on the precursor, through hydration of the oxidant, or both.

Scheme 3. Reactivity of [Cp*Ir(bipy)X]BF$_4$ complexes with periodate.

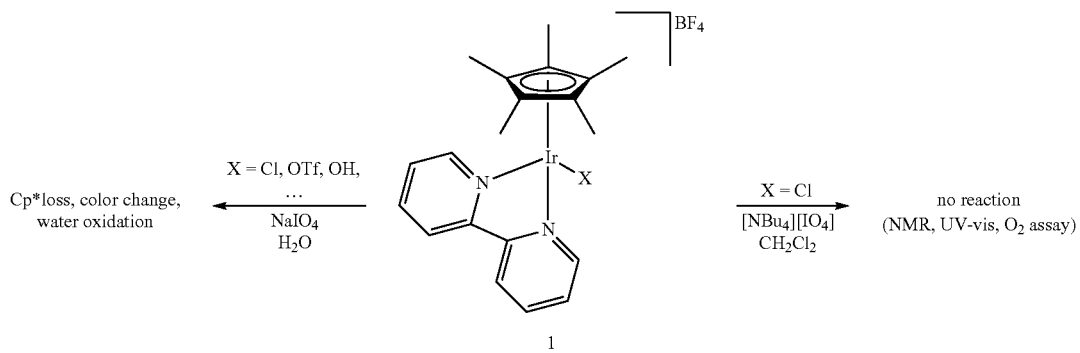

1

When a 1:1 mixture of 1 and 2 was reacted with excess NaIO$_4$ in water, the Cp* peak of 1 quickly disappeared from the $^1$H-NMR spectrum as in the absence of 2, but the Cp* peak of 2 also started to decrease over time with more HOAc being formed. This mutual attack on the otherwise inert 2 by oxidized 1 reflects the CH-oxidation ability of these catalysts, and shows that bimolecular pathways may also play a role in the initial precursor oxidation. This observation is important with regards to traces of easily oxidizable iridium impurities potentially carried through to catalytic mixtures from the synthesis.

Cp*Ir$^{III}$ complexes bearing the more strongly donating LX-type pyalc ligand (3, Scheme 4) yielded more rapid color changes with an apparent first-order rate constant of ~0.4 s$^{-1}$ when oxidized with NaIO$_4$, about five times faster than the bipy-based precursor.

Scheme 4. Oxidation of orange [Cp*Ir(pyalc)OH] to a blue species.

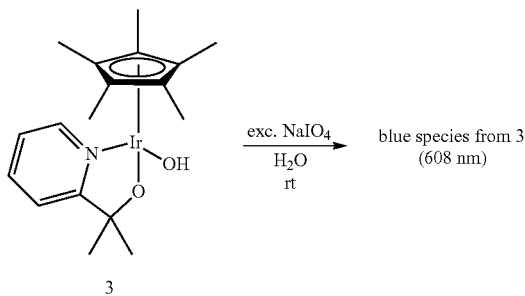

Figure 4A:
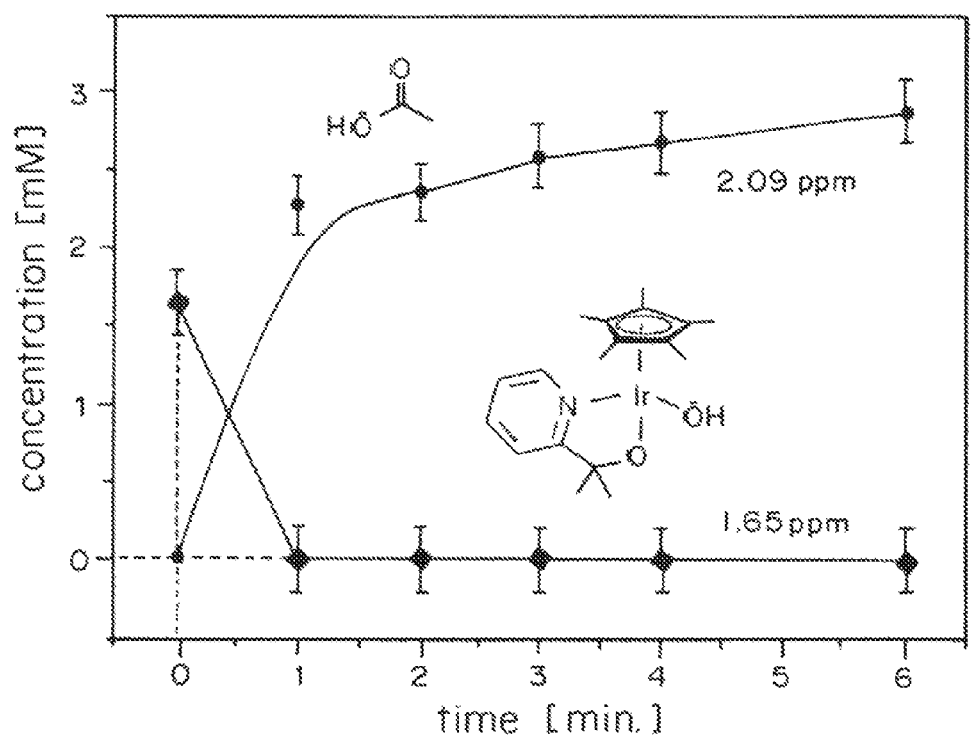
FIG. 4A is a $^1$H-NMR time-course of the reaction of 3 at 2 mM with 100 mM NaIO$_4$ in H$_2$O as measured from samples quenched with NaHSO$_3$+sodium d$_4$-trimethylsilylpropionate (20 mM) in D$_2$O [concentration (mM) v. time (min)].
Figure 4B:
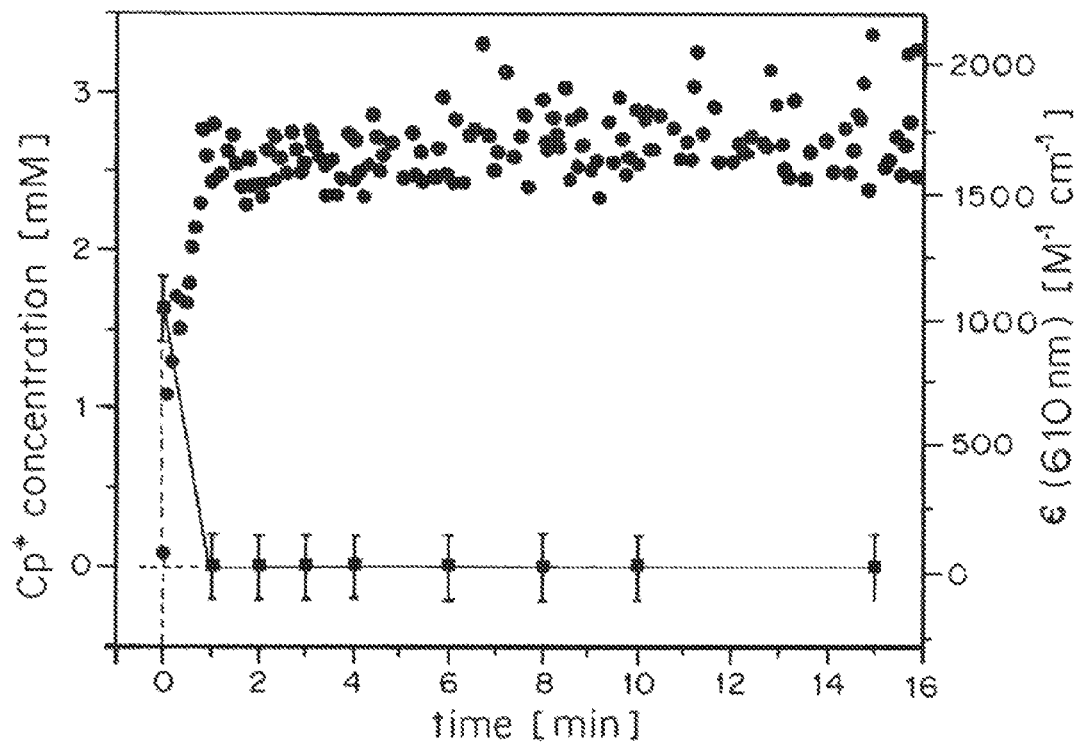
FIG. 4B is a comparison with UV-Vis kinetics of the same reaction monitored at 610 nm, [Cp* concentration (mM) v. time (min)] demonstrating the kinetic correlation of oxidative Cp* removal and formation of the blue species that is the active catalyst.

The corresponding blue species with a $\lambda_{max}$≈608 nm was found to persist for days even after complete exhaustion of oxidation potential in solution. Oxidative Cp* loss was also quicker for 3 than for 1, again liberating~1.8 eq. HOAc/[Ir] without any other detectable organic species in solution (FIG. 4). Small and broadened ligand peaks remained visible in the aromatic region of the NMR spectrum as in the case of the 1.

Figure 5:
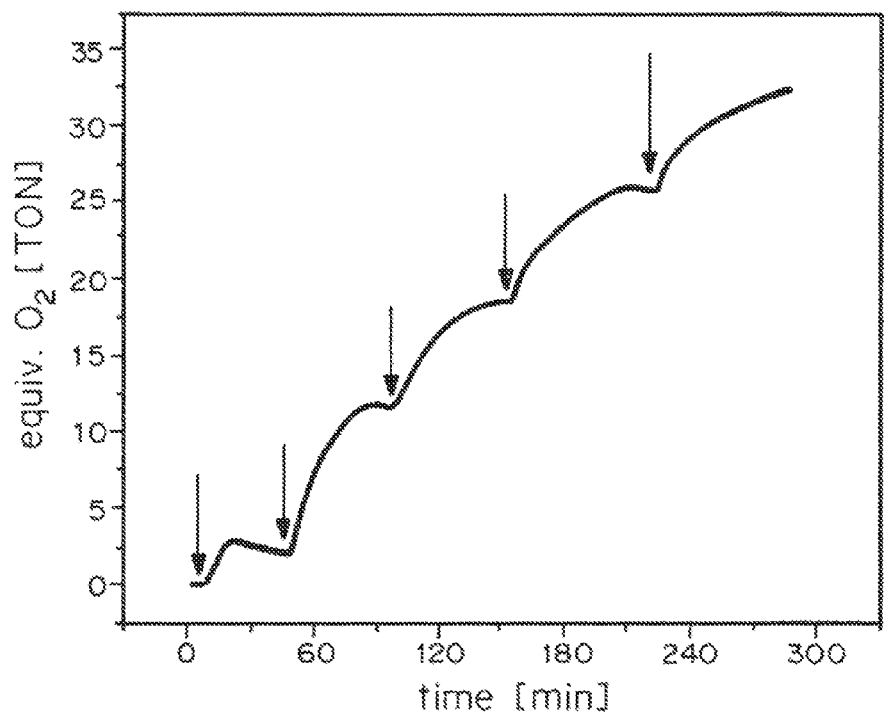
FIG. 5 is a graph showing the water-oxidation activity of 3 at 4 μM during multiple additions of 34 equivalents NaIO$_4$ in H$_2$O as measured by Clark-type electrode in the liquid phase (rates slightly decrease due to successive dilution) showing increased O$_2$ evolution efficiency after initial activation (equiv. O$_2$ [TON] v. time (min)].

To test whether the stable blue species produced from 3 may re-enter the catalytic cycle once formed, O$_2$ evolution was monitored during multiple additions of aqueous NaIO$_4$ to a dilute solution of 3 (FIG. 5). Under the conditions applied, an initial induction period of about 2 min before O$_2$ evolution set in was observed, which may shorten to a minimum of ~10 seconds at higher concentrations. Thereafter, production of ~3 TON of O$_2$ quickly occurred. Repeated additions of the same amount of NaIO$_4$ to the same solution then caused immediate O$_2$ production with increased water-oxidation efficiencies of average 7.5 TON to O$_2$ over at least 4 cycles. Such sustained oxidation activity has been described for various Ir-precursors oxidized with Ce$^{IV}$, but was interpreted as oxidative loss of all ligands and decomposition to IrO$_x$ NPs as the true active catalyst. This possibility is excluded based on the observed ligand effect in the UV-Vis and our dynamic light scattering results which showed the system 3+NaIO$_4$ to be homogeneous.

Similarly, the catalytic CH-oxidation activity of 3 could also be sustained during repeated water-oxidation, and cumulating turnover numbers were obtained upon multiple additions of ethylbenzene-sulfonate (EBS) and NaIO$_4$ to an aqueous solution of 3 (Scheme 5 and Table 1).

Scheme 5. Methylene oxidation of ethylbenzene-sulfonate (EBS) to acetophenone-sulfonate (APS) with NaIO$_4$ catalyzed by 3.

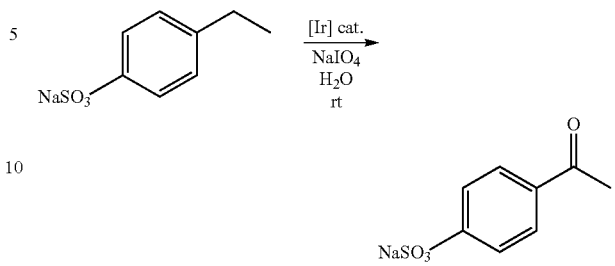

TABLE 1

Activity of 3 at 0.5 mM in catalytic EBS oxidation (scheme 5) upon multiple additions of substrate and oxidan.

| EBS | NaIO$_4$ | reaction time | TON to APS |
|---|---|---|---|
| 20 eq. | 200 eq. | 30 min | 13 (±2) |
| 40 eq. | 400 eq. | 60 min | 32 (±2) |
| 60 eq. | 600 eq. | 90 min | 41 (±2) |
| 80 eq. | 800 eq. | 120 min | 52 (±2) |

These observations have at least two important implications. The Cp*-free blue molecular species formed after initial oxidation is either part of or directly connected to the catalytic cycle. Furthermore, the fact that an induction period is only initially observed and that unperturbed performance occurs upon re-oxidation suggests that intramolecular loss of the Cp* ligand precedes any intermolecular turnover, and is thus a precursor activation step rather than a decomposition pathway as previously suggested.

Figure 6:
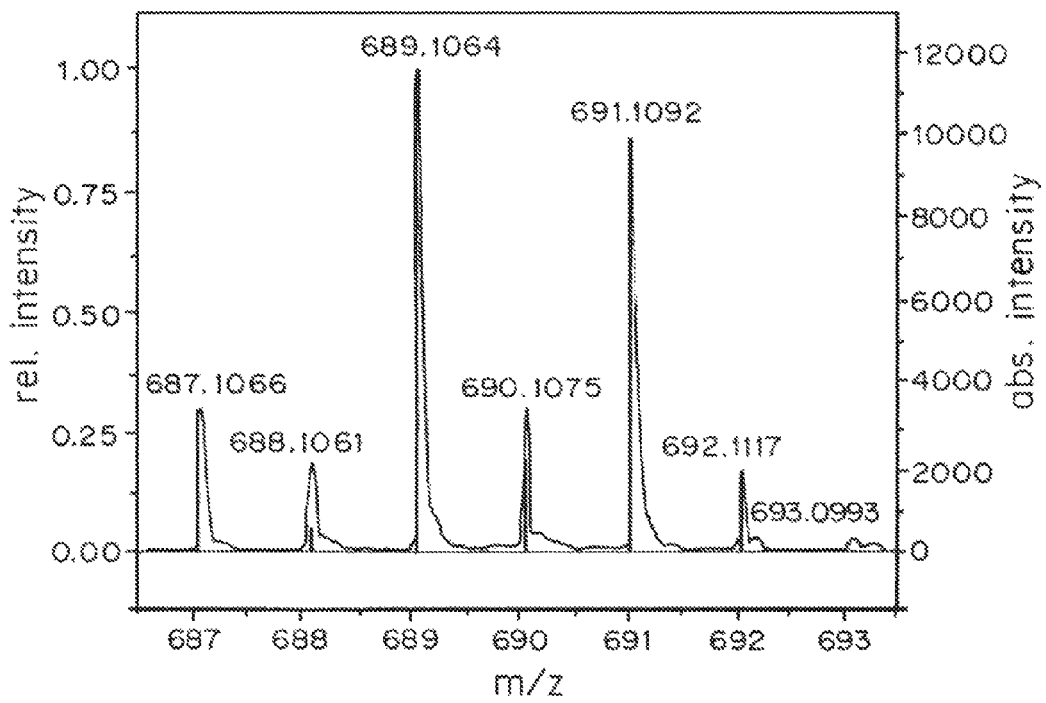
FIG. 6 is a section of the experimental MALDI-TOF-MS (+) spectrum of a sample of 3 oxidized with NaIO$_4$ as obtained from α-cyano-4-hydroxycinnamic acid matrix (curve and values), and simulation for [Ir$^{III}_2$(pyalc)$_2$(O)$_2$H]$^+$=C$_{16}$H$_{21}$Ir$_2$N$_2$O$_4{}^+$, a reduced derivative of the blue species in solution.

Although remarkably robust in solution, isolation of the blue species of oxidized 3 from its native aqueous solution in pure form proved difficult, and more detailed characterizations were thus performed on the solution. MALDI-TOF-MS(+) analysis of partially oxidized 3 from a reducing matrix showed several [Cp*Ir(pyalc)]$^+$+[O] species indicating successive oxygenation of the precursor, as well as Cp*-free dimers with iridium in the (III) oxidation state (FIG. 6). Simulation of these peaks agreed with their assignment as [Ir$_2$(pyalc)$_2$(O)$_2$H]$^+$ at a high accuracy of 44 ppm. Such dimers would be fully consistent with all previous observations on oxidative Cp* loss under preservation of the chelate ligand, and similar bis-µ-hydroxy aqua-dimers of iridium are known to be blue with a $\lambda_{max}$≈590 nm in the (IV) oxidation state. No iodine-containing adducts were detected by MS and no peaks above 1200 m/z were observed, excluding the presence of higher nuclearity clusters or nanoparticles consistent with previous light scattering results.

Figure 7:
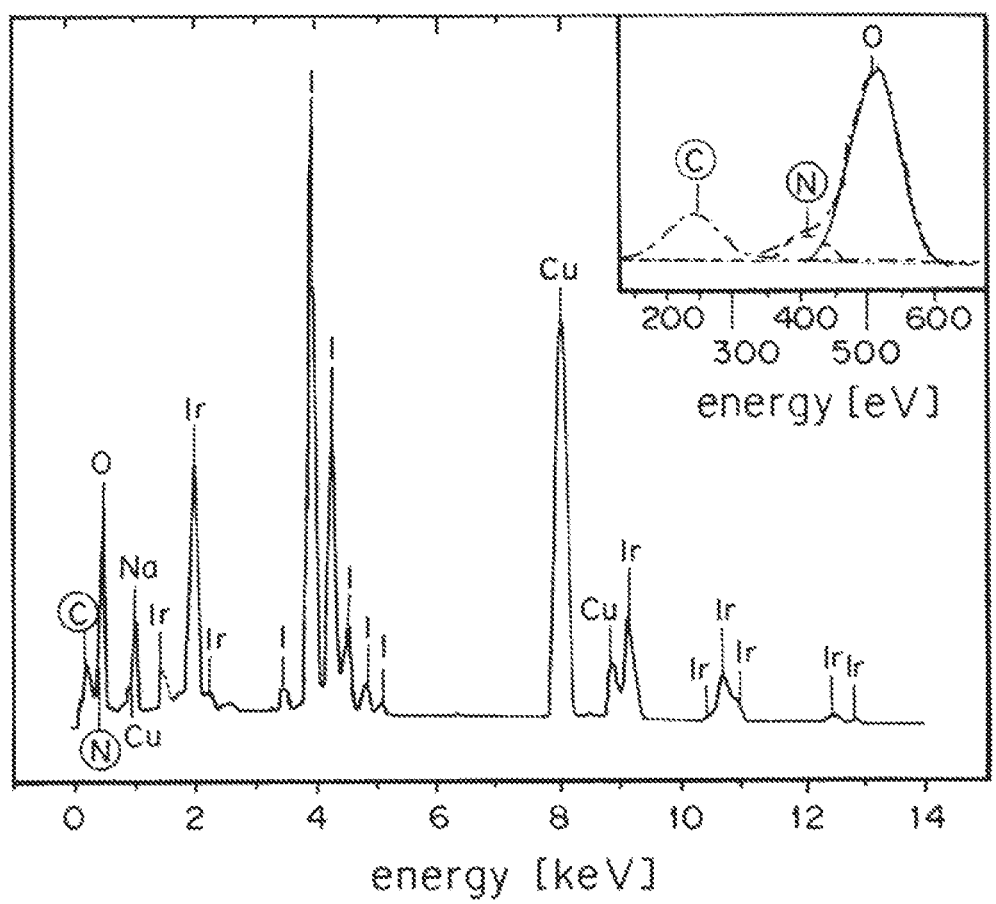
FIG. 7 is an EDX spectrum (200 kV) of a sample of vacuum-dried blue species from 3 (including the reduced form of the oxidant NaIO$_4$) showing the presence of C, N, O, Na, I, and Ir (Cu signals arise from the TEM grid) with deconvoluted peaks of the C/N/O region shown in the insert proving retention of the chelate ligand in oxidatively activated 3.
Figure 8A:
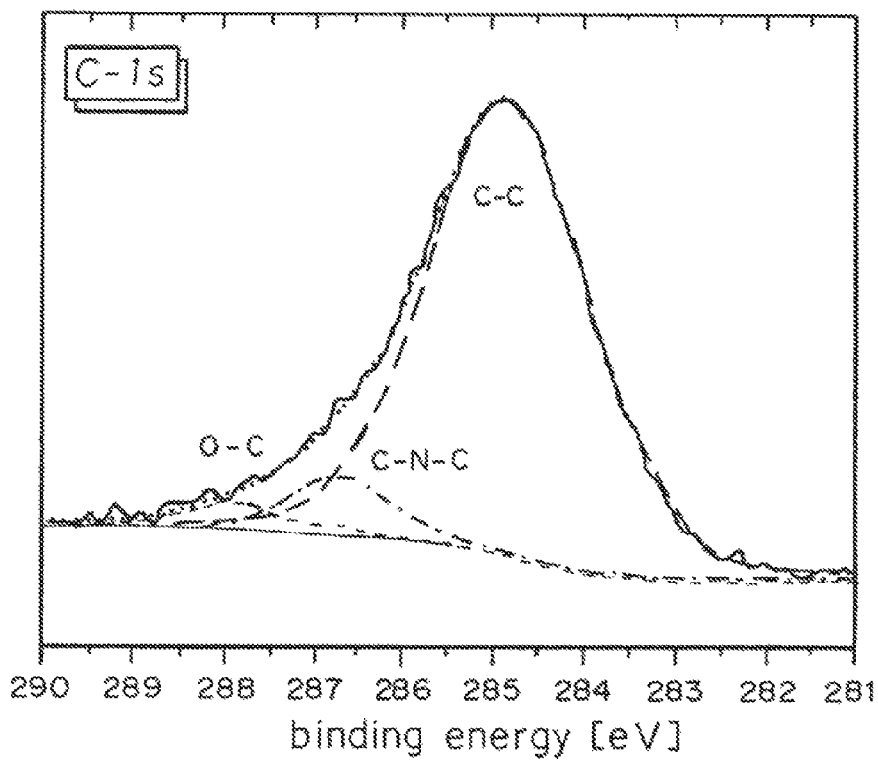
FIG. 8A is the Carbon-1s section of the XPS spectrum (Al Kα radiation) of a sample of vacuum-dried blue species from 3 (including the reduced form of the oxidant NaIO$_4$).
Figure 8B:
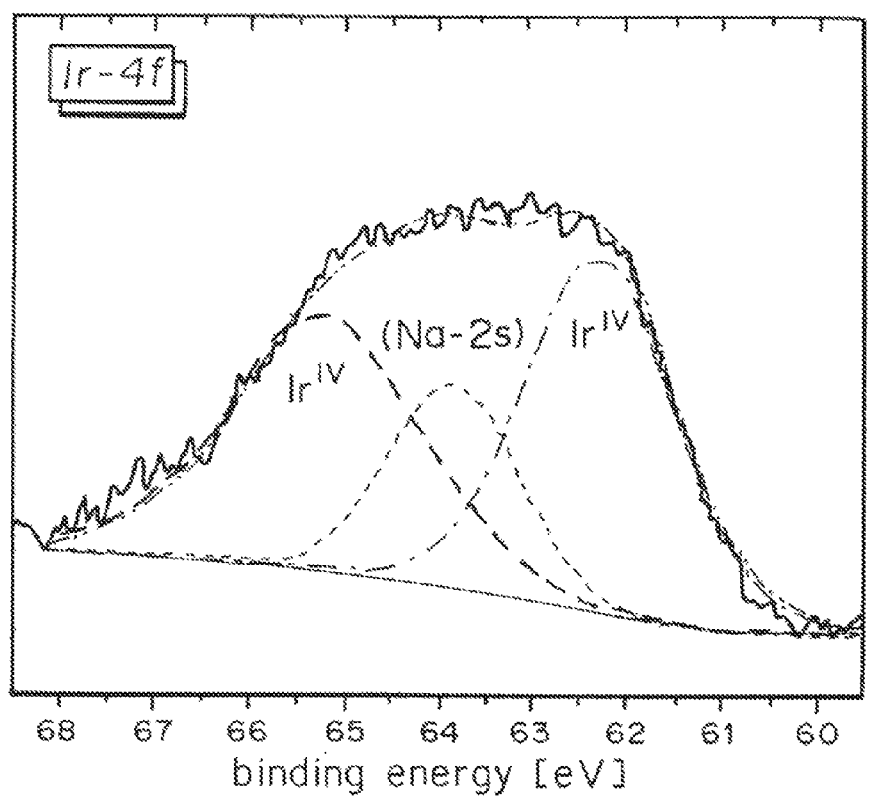
FIG. 8B is the iridium-4f section of the XPS spectrum (Al Kα radiation) of a sample of vacuum-dried blue species from 3 (including the reduced form of the oxidant NaIO$_4$).

TEM-EDX analysis showed the presence of both carbon and nitrogen in a sample of fully oxidized 3 dried to a powder in high vacuum (FIG. 7). Although carbon was not securely quantifiable due to background from adventitious carbon, a clear 1:1 ratio of N to Ir was found as further indication for the retention of the chelate ligand in the blue species consistent with the MS analysis. When exposed to the focused electron beam for longer times, the material progressively decomposed to form ~7 Å domains of rutile IrO$_2$. XPS analysis of the same sample on ultra-pure gold also showed N-1s and C-1s signals, the latter comprising sp$^2$ carbon (284.8 eV), ortho-nitrogen carbon (286.7 eV), and $sp^a$ carbon neighboring oxygen (287.9 eV) (FIG. 8A). Consistent with the quantification by EDX, an approximately 1:1 ratio of N to Ir was found again. The Ir-4f doublet observed at 62.4 eV and 65.3 eV, although overlapping with the Na-2s signal from the oxidant at 63.9 eV, is fully consistent with iridium being exclusively in the (IV) oxidation state (FIG. 8B). The solid material retained its blue color under brief x-ray irradiation, suggesting retention of its native oxidation state during the course of the analysis. Although some oxo-centered acetate trimers and nitrido-centered sulfate trimers of iridium are known to be remarkably stable in (III)-(IV) mixed-valent states, the presence of stoichiometric amounts of $Ir^{III}$ in the blue species of 3 can be ruled out by the lack of any distinguishable peak in the 60-61 eV region in the XPS analysis.

Complete departure of Cp* from the metal with retention of the chelate ligand would leave each iridium with four open sites, which would most likely be occupied by oxo, hydroxo, or aqua ligands under oxidative conditions in water. Mononuclear metal-aqua ion chemistry is well established even for the less oxophilic late transition metals and some polynuclear oxy-bridged aqua-clusters are also known. $^{17}$O-NMR can be used to probe the solution chemistry of such aqua- and polyoxo-ions, because the quadrupole-broadened resonances and the large shift range of the $^{17}$O nucleus (>1000 ppm) make it virtually insensitive to paramagnetic effects in solution, providing a convenient probe for metal-oxo compounds across different oxidation states.

Complex 3 dissolved in $^{17}$OH$_2$ (10 mM, pH~9) showed one broadened signal (w½=290 Hz) at 174 ppm originating from the $Ir^{III}$-OH exchanging with solvent. The strong trans-effect of Cp* on monodentate ligands in the otherwise extremely slow-exchanging $d^6$ $Ir^{III}$ aqua-complexes is well documented and in this case enhanced further by the π-basic pyalc ligand. NaIO$_4$ in $^{17}$OH$_2$ (200 mM, pH~5) gives a characteristic, broad signal from 210-260 ppm (centered at 236 ppm, w½=2300 Hz) owing to quadrupolar coupling of the $^{17}$O with $^{127}$I overlaid with various hydration equilibria.

Figure 9:
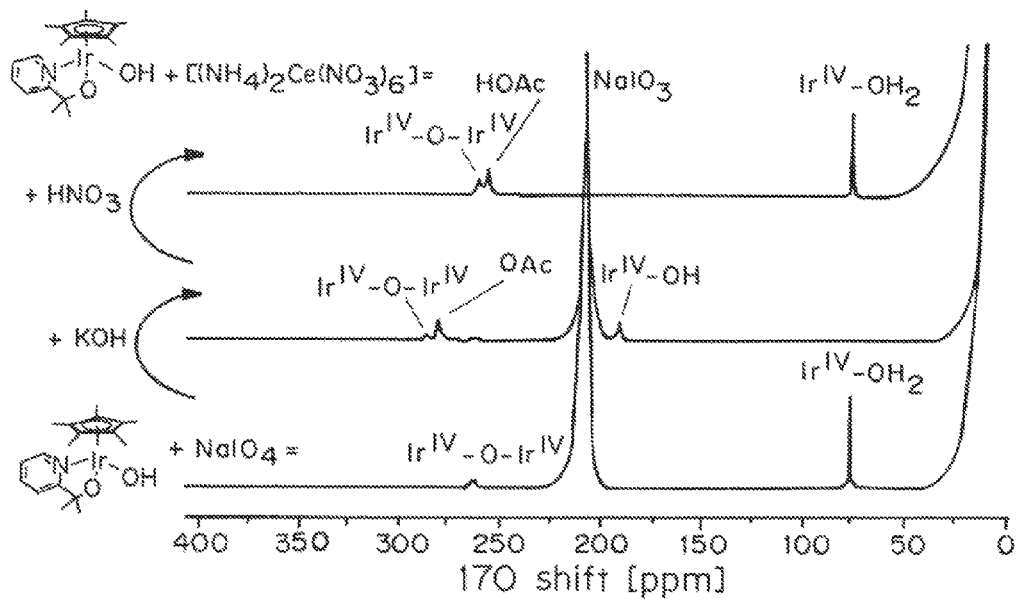
FIG. 9 is a $^{17}$O-NMR spectrum of 3 (10 mM) oxidized with NaIO$_4$ (200 mM) in 10% $^{17}$OH$_2$ as prepared (pH~5, bottom trace), basified with KOH to pH~12 (middle trace), and re-acidified with HNO$_3$ to pH~1 (top trace). 3 oxidized with CAN instead of NaIO$_4$ under otherwise identical conditions yielded the same spectrum as the acidified periodate sample (top trace).

Stable blue solutions of 3 oxidized with periodate in $^{17}$OH$_2$ showed none of the precursor or periodate peaks, but three new signals instead (FIG. 9). The dominant peak at 207 ppm (w½=400 Hz) was identified as NaIO$_3$ by comparison with an authentic sample, providing spectroscopic evidence for periodate acting as a net 2-electron acceptor when driving oxidation catalysis. The sharp peak at 77 ppm (w½=35 Hz) is consistent with an $Ir^{IV}$-aqua unit, while the broader signal at 265 ppm (w½=340 Hz) lies in the shift region characteristic for μ-oxo ligands. A quantitative $^{17}$O-NMR spectrum showed a clean 1:2 ratio of μ-oxo to aqua peak area. Thus, considering the observation of dimeric species in the MS and the all-$Ir^{IV}$ state as derived from XPS the most plausible formulation for blue, activated 3 is $[Ir^{IV}(pyalc)(H_2O)_2(\mu-O)]_2^{2+}$. In order to ascertain the assignment of the 77 ppm peak as coordinated water, the solution of oxidized 3 prepared in $^{17}$OH$_2$ was basified with KOH to pH~12. No visible color changes occurred, ruling out reduction of the iridium. As can be seen in FIG. 9, the aqua peak shifted almost completely to 190 ppm (w½=170 Hz), assignable to the corresponding $Ir^{IV}$-OH. The μ-oxo peak also moved downfield by about 20 ppm as a result of the deprotonation, substantiating the notion that both functionalities are part of the same molecule. Re-acidifying the sample with HNO$_3$ regenerated the initial spectrum, reforming all $Ir^{IV}$-OH$_2$ and shifting the μ-oxo peak back to its original position. The missing iodate peak in the acidic sample is due to the known rapid exchange with solvent water at low pH, which is also reflected in the broadened free water peak at 0 ppm. The observation that neither the Ir—O—Ir nor the Ir—OH$_2$ signals experienced measurable changes in their line shapes at low pH indicates surprisingly low exchange rates of both functionalities at a $d^5$ metal center, which probably arises from electronic coupling in the (IV)-(IV) dimer. Temperature variation between 10-80° C. did also not cause any changes in the $^{17}$O spectrum either, although some dark precipitate formed above 60° C. at the expense of signal intensity. The fact that no noticeable line broadening occurred until thermal decomposition speaks to the remarkably high stability of the $Ir^{IV}$ μ-oxo dimer containing the pyalc ligand. Upon raising the pH of the blue solution of 3 oxidized with NaIO$_4$, acetate appeared in the $^{17}$O-NMR spectrum at 280 ppm and acetic acid persisted at 255 ppm$^{90}$ after re-acidifying (as verified by spiking with authentic HOAc). The fact that (H)OAc was initially not visible in the $^{17}$O-NMR in solutions of oxidized 3 (but clearly observable by $^1$H and $^{13}$C-NMR, see above) suggests that its formation through Cp* oxygenation is too fast to allow for $^{17}$O incorporation from the solvent. O-exchange reactions of carboxylic acids in water are known to be very slow at neutral pH but are both acid- and base-catalyzed, so (H)OAc only becomes visible in the $^{17}$O spectrum upon post-synthetic pH variation. No other oxycarbon species were detected by $^{17}$O-NMR.

Importantly, when 3 was oxidized with CAN instead of NaIO$_4$ in $^{17}$OH$_2$, exactly the same spectrum was obtained as after addition of HNO$_3$ to the sample oxidized with NaIO$_4$ (FIG. 9, top trace). This demonstrates that the formation of the blue $Ir^{IV}$ μ-oxo dimer is not influenced by the nature of the chemical oxidant at least in this particular case.

To further affirm the presence of a bis-μ-oxo structure the blue species of oxidized 3 was analyzed by Raman spectroscopy. The bis-μ-oxo di-metal unit is a common motif in the active sites of oxidative metalloenzymes and through detailed analyses of synthetic bis-μ-oxo dimers of Mn, Fe, Co, Ni, and Cu it has been shown that planar M-O/O-M cores exhibit characteristic Raman-active stretches at ~550-750 cm$^{-1}$, providing a convenient distinction from other metal-oxo functionalities such as mono-μ-oxo (<500 cm$^{-1}$), terminal oxo (>900 cm$^{-1}$), or peroxo units (750-850 cm$^{-1}$).

Figure 10A:
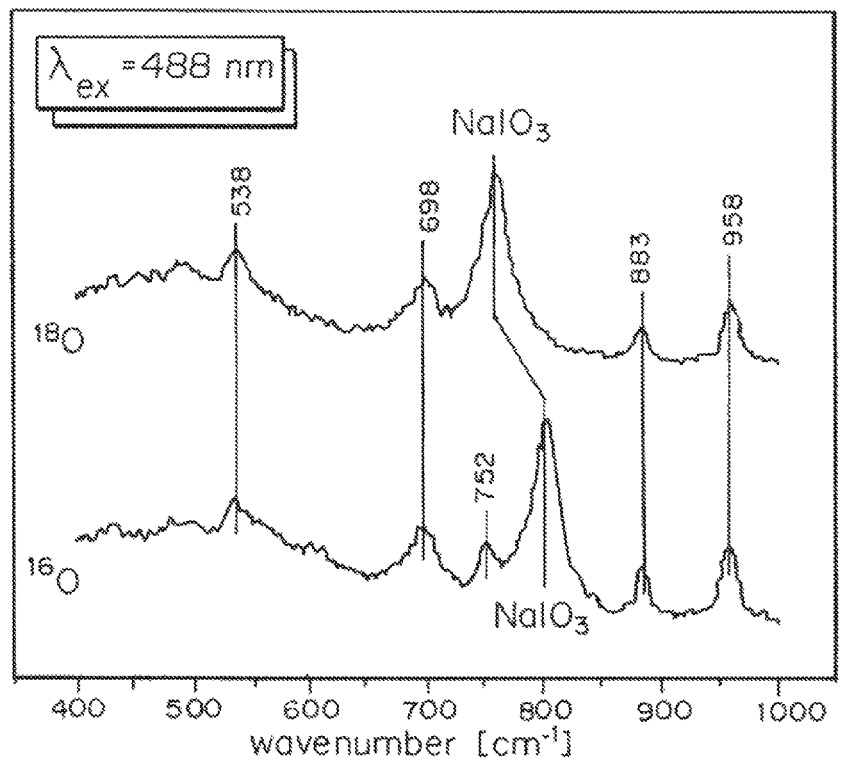
FIGS. 10A and 10B are resonance-Raman spectra of solutions 3 (5 mM) oxidized with NaIO$_4$ (200 mM) in $^{16}$OH$_2$ (bottom traces) and 95% $^{18}$OH$_2$ (top traces) after 30 minutes reaction time as obtained with different excitation energies (left: 488 nm argon-ion laser at 50 mW, right: 660 nm diode laser at 17 mW). The spectroscopic features together with the observed $^{18}$O isotope shifts strongly support a bis-μ-oxo di-iridium unit in the blue species from 3.

Raman spectra of solutions of oxidized 3 showed the presence of iodate at its expected position of 800 cm$^{-1}$ irrespective of the excitation wavelength used. Resonance-enhancement was observed with either 488 nm or 660 nm laser excitation to give different sets of molecular signals in the 400-900 cm$^{-1}$ fingerprint region characteristic for oxo compounds. Except iodate, all peaks observed with 488 nm excitation were found to be insensitive to $^{16/18}$O substitution (FIG. 10A), consistent with this wavelength being in a regime of pyalc-based electronic transitions that predominantly yield resonance-enhancement of ligand-based vibrational modes. This observation is also further experimental support for retention of unmodified (i.e. non-oxygenated) chelate ligand in the blue Cp*-free species obtained from oxidation of the corresponding Cp*$Ir^{III}$(chelate) precursor.

Figure 10B:
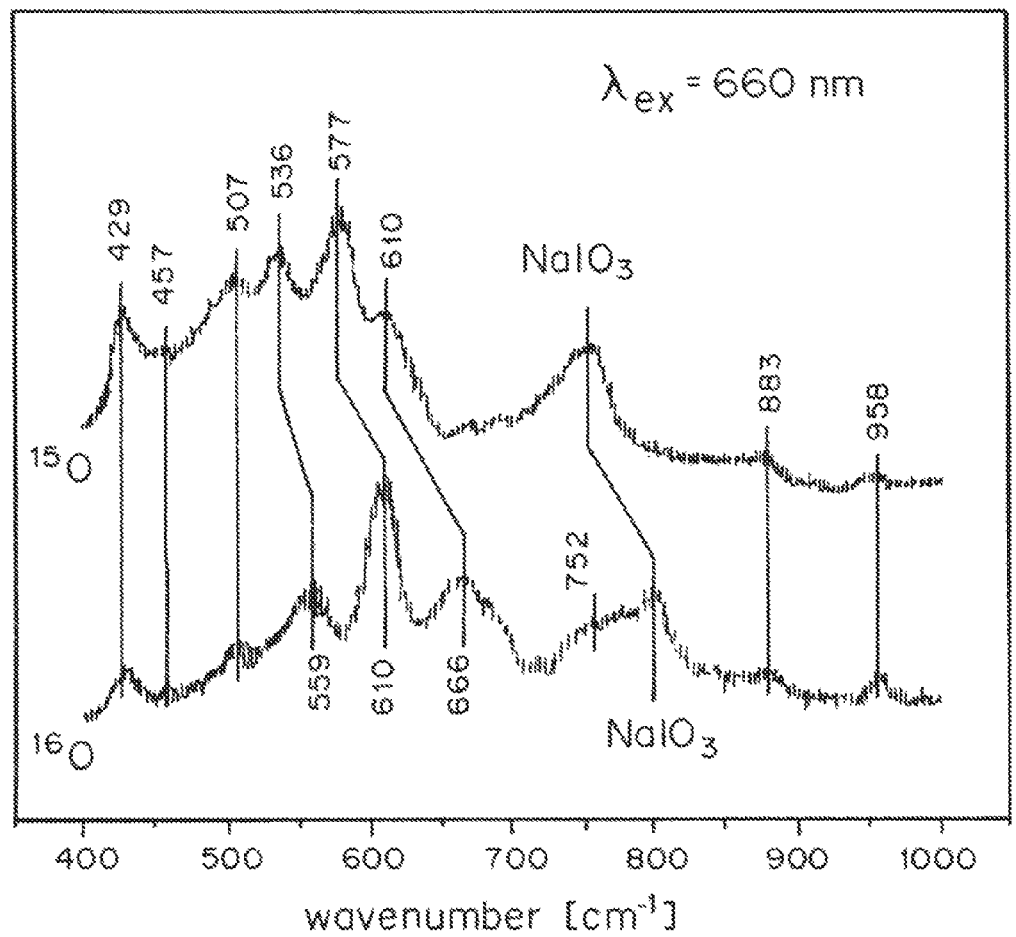

Excitation in the lower-energy tail of the $Ir^{IV}$-oxo transitions at 660 nm yielded different resonance-enhancement to give Raman peaks that were not visible with 488 nm excitation (FIG. 10B). Three major new features were located at 559, 610, and 666 cm$^{-1}$, exactly in the regime expected for a bis-μ-oxo di-metal core. Consistently, upon assembly in $^{18}$O H$_2$ these peaks showed isotopic shifts of 56, 33, and 23 cm$^{-1}$ respectively, proving that these modes originated from oxo functionalities. Three common features at 752, 883, and 958 cm$^{-1}$ were observed with both $\lambda_{ex}$ but no other peaks shifted with $^{18}$O substitution.

To demonstrate that Cp* is not needed for homogeneous iridium-catalyzed oxidations the corresponding (cod)Ir$^I$ complexes (cod=cis,cis-1,5-cyclooctadiene) were prepared with the bipy (4) and pyalc (5) ligands as alternative catalyst precursors (Scheme 6).

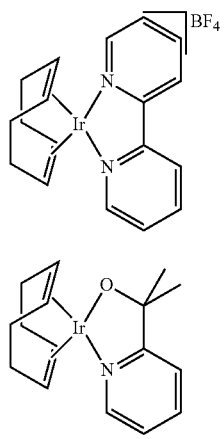

Their oxidation should occur very readily, and although some high-valent cod complexes of iridium are known it is rather unlikely that the L$_2$ hydrocarbon ligand cod remains bound to the iridium under conditions where the more strongly donating L$_2$X ligand Cp* is lost.

Oxidation of the (cod)Ir$^I$ complexes 4 and 5 with NaIO$_4$ in H$_2$O indeed yielded solutions with UV-vis spectra very similar to the ones obtained from the corresponding Cp*Ir$^{III}$ precursors 1 and 3, respectively. Although the kinetics appeared slightly different, the final $\lambda_{max}$ values were identical for a given chelate ligand (FIG. 11), indicating that irrespective of the sacrificial hydrocarbon ligand in the precursor the same $[Ir^{IV}(chelate)(aqua)_x(oxo)_y]_z^{n+}$ species had assembled under oxidative conditions. Furthermore, the blue species from 4 eventually decayed to a yellow species in solution as it was the case when using 1, whereas the blue species formed from 5 persisted as in the case of 3. These results demonstrate that Cp* is not needed for oxidation catalysis, and that other sacrificial placeholder ligands may be used alternatively as long as one oxidation-resistant chelate ligand is used to prevent the formation of IrO$_x$ material. The retained chelate ligand is clearly the most important parameter for tuning the robustness and rate of catalytic water-oxidation, selectivity in CH-oxidation catalysis, and for attachment to surfaces and other aspects of incorporation of these highly active catalysts into electrochemical devices and light-harvesting arrays for solar fuel production.

Example 3. Oxygen Yield of Ir$^{IV}$ Homogeneous Catalyst

Oxygen was detected with a Clark electrode using a custom made zero-headspace 10 mL glass cell, water jacketed for constant temperature. A Teflon cap through which the Clark electrode membrane contacted deionized water (adjusted to pH 2.5 using nitric acid) also held a catalyst-coated nanoITO film on FTO-coated glass sample that was submerged in the cell. Catalyst-loaded samples were prepared similarly to those used for electrochemistry, except with a 1.6 cm2 geometric surface area. The Clark electrode was allowed to stabilize while stirring the deionized water solution for one hour prior to injection with an oxidizing solution of freshly prepared NaIO4 in deionized water. Catalyst response and O2 generation occurred immediately, without any lag phase.

A typical experiment, used 25 μL of 0.25 M NaIO4 in deionized water. The oxygen content in the cell was monitored until oxygen evolution ceased, which for a loading of around 50 nmol of iridium (corresponding to a nanoITO film 11 μm thick) took approximately 90 minutes. Data were collected while stirring the solution to ensure steady state oxygen readings. A sample was used that was loaded with approximately 49.1 nmol of iridium. Decreasing the amount of catalyst on the surface by decreasing nanoITO thickness, higher turnover numbers and turnover frequencies were achieved. This is likely due to both a larger ratio of oxidant to catalyst and a higher percentage of the catalyst easily accessible to the solution without having to diffuse oxidant through the mesoporous nanoITO film.

Figure 12A:
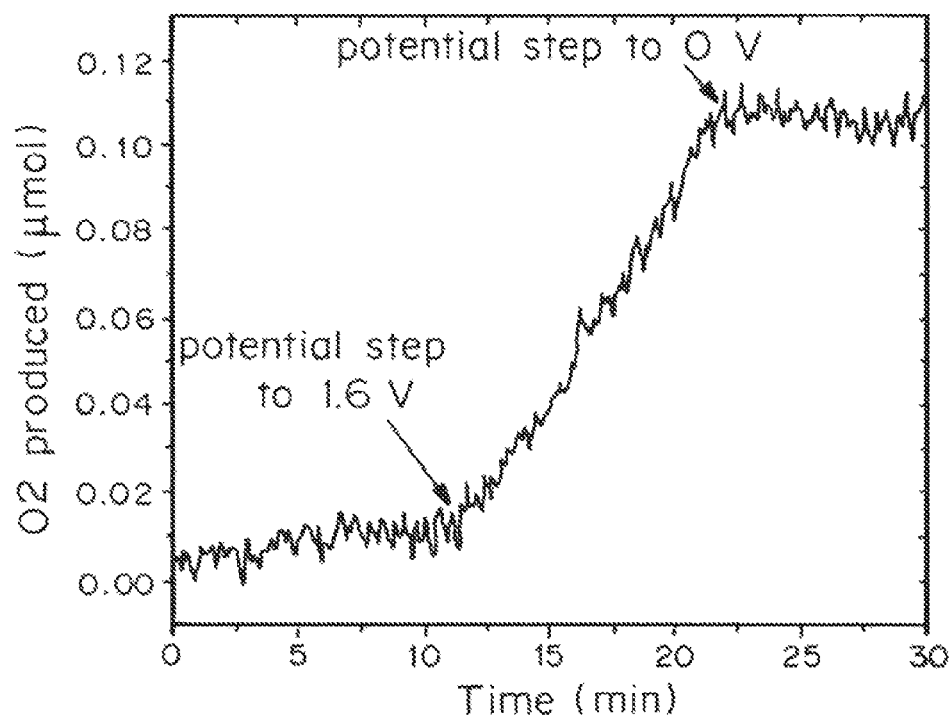
FIG. 12A is a graph showing the amount of oxygen (μmol) produced over time (min).
Figure 12B:
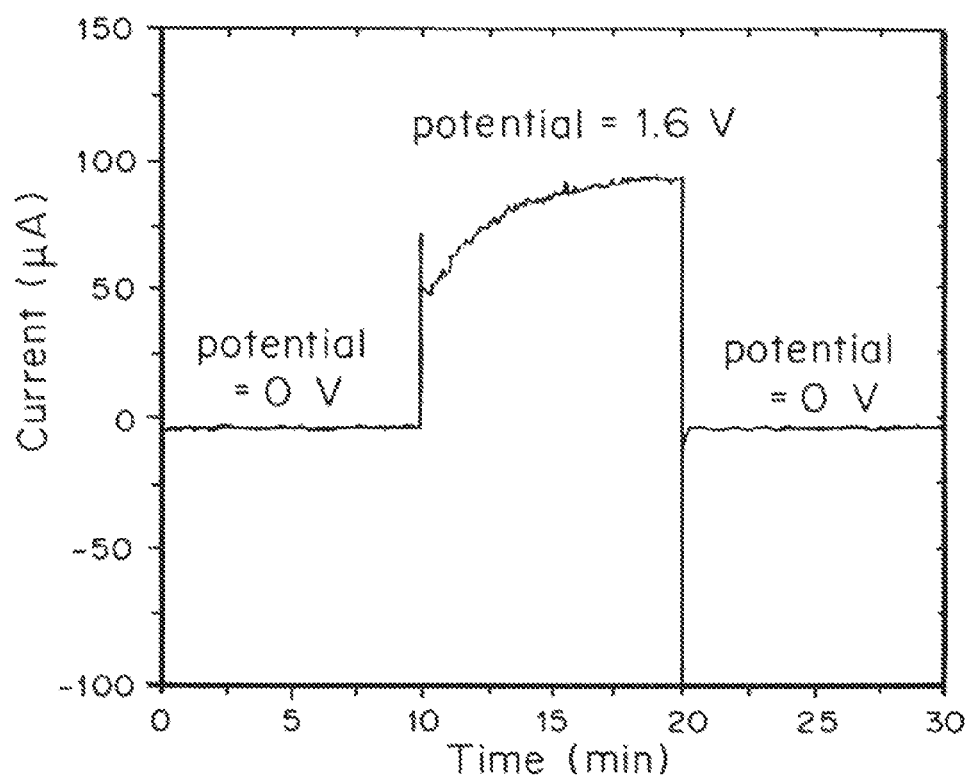
FIG. 12B is a graph showing the current passed by electrolysis during the same experiment. As soon as the potential (vs. NHE) is stepped from 0 V to 1.6 V, solution oxygen levels begin to increase steadily until the potential is stepped back to 0 V. The charge passed (45 mC) predicts a yield of 0.12 μmol, and the measured yield is approximately 0.11 μmol, indicating Faradaic efficiency of ≥92%.

$[Ir^{IV}(LX)(H_2O)_2(\mu-O)]_2^{2+}$ can be used as homogenous electrocatalyst for the oxidation of water. After formation, with no further modification, electrolysis of the aqueous solution at a gold electrode held at 1.6 V vs. NHE results in high sustained current concomitant with oxygen production as measured by Clark electrode. The oxygen yield is virtually quantitative, indicating that at this potential the catalyst operates with close to 100% Faradaic efficiency (FIG. 12). Notably, zero water-oxidation activity is observed when subjecting the non-preoxidized precursors to the same conditions.

Figure 17A:
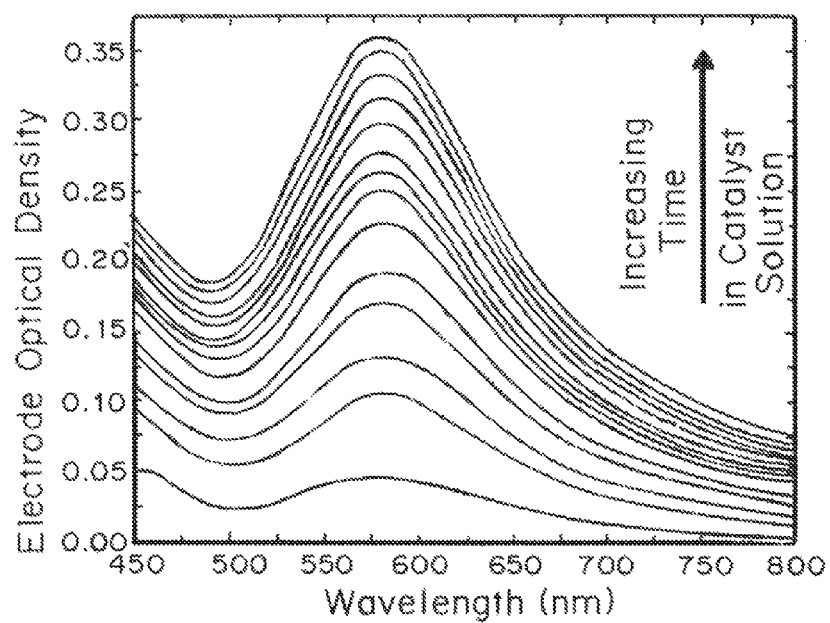
FIG. 17a is a graph showing the optical density of an electrode measured after increasing time immersed in catalyst solution at room temperature.
Figure 17B:
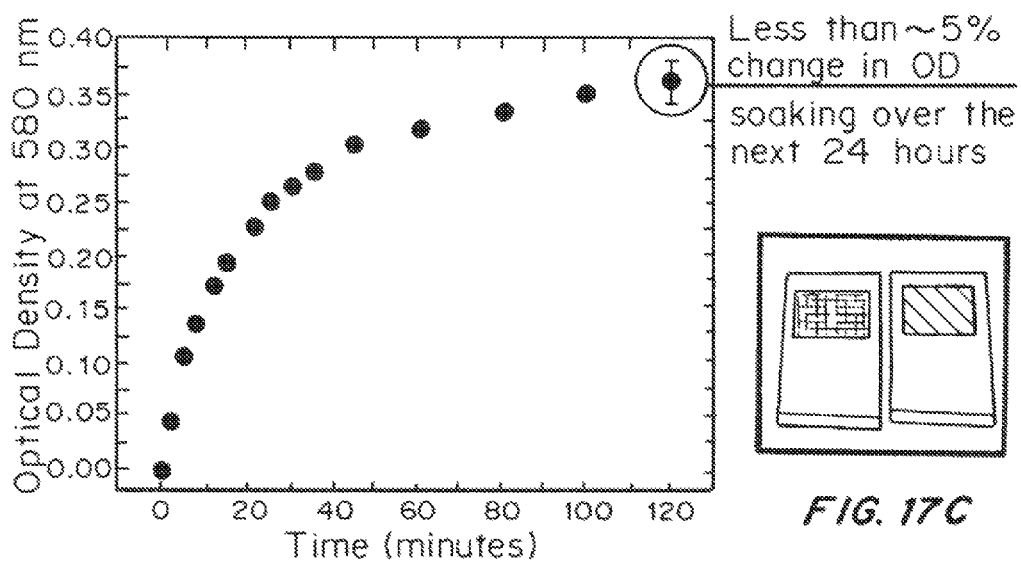
FIG. 17b is a graph showing the optical density at 580 nm for the electrode as a function of immersion time.
Figure 17C:
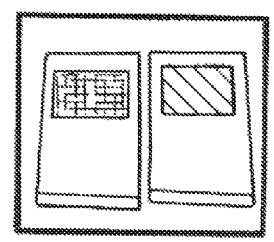
FIG. 17c is a photograph of an electrode before (left) and after (right) immersion in catalyst solution for two hours.

Example 4. Ir$^{IV}$ Catalyst Binds to Oxide Substrates without External Stimulus $[Ir^{IV}(LX)(H_2O)_2(\mu-O)]_2^{2+}$ binds to many oxide materials as a monolayer by simple immersion for a few hours at room temperature without any other external stimulus as demonstrated on nanoporous tin-doped indium oxide (ITO). Electrochemical characterization for a monolayer catalyst requires a high surface area and a conductive substrate making nanoporous ITO amenable for this immediate application. FIG. 17a shows UV-Vis absorption spectra with increasing time as a substrate of ITO nanoparticles coated on a conductive FTO-coated glass electrode is immersed in a solution of the activated catalyst, with the corresponding data shown in the time-domain in FIG. 17b. FIG. 17c shows a shift in peak absorption wavelength of the catalyst when bound to the surface compared to when in solution that is consistent with the catalyst being bound by water elimination.

This procedure effectively allows functionalization of electrode materials with a highly active electrocatalyst material through an exceptionally simple coating process. The types of substrates on which the catalyst can be deposited varies, and includes conductive oxides such as ITO, and photocatalytic oxides such as titanium dioxide, iron oxide, and tungsten trioxide. All of the slides in FIG. 18 were washed and soaked in water after the initial deposition, and we find that the bound catalyst is essentially unaffected over a wide pH range and in a number of organic solvents, indicating high chemical stability.

The catalyst bound on the surface of an oxide electrode exhibits very high electrocatalytic activity in water-oxidation. Electrodes functionalized with the catalyst material have record low overpotentials for water-oxidation, around as low as 160 mV with 0.5 mA/cm$^2$ current at the working electrode for samples with up to 18 μm thick porous nanoITO coatings. This is tunable down to lower values by increasing the surface area of the scaffold and thus the loading of the catalyst, in this case by increasing the thickness of the nanoporous ITO layer. A working electrode of iridium catalyst on nanoporous ITO coating an FTO/glass substrate under sustained water-splitting conditions at 1.4 V vs. NHE produced visible bubbles of evolved oxygen.

Figure 13:
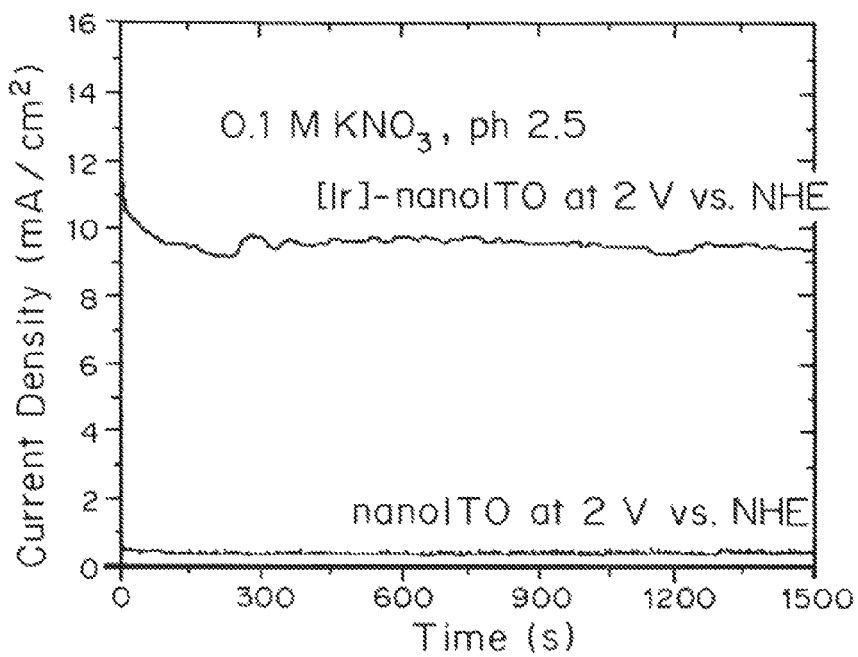
FIG. 13 is a graph of a 25 minute high-potential water electrolysis showing high stability at approximately 9-10 mA/cm$^2$ current density with 2 V applied potential vs. NHE (pH 2.5 in 0.1 M KNO$_3$).
Figure 14:
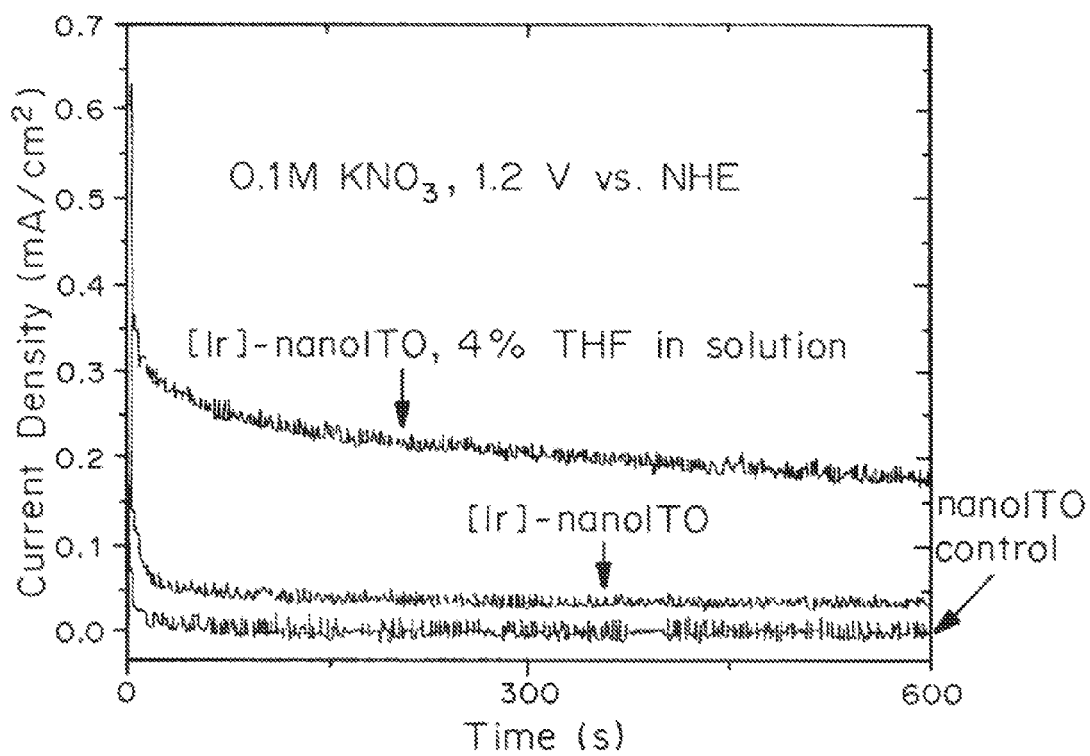
FIG. 14 is a graph showing room-temperature electrode-driven carbon-hydrogen bond oxidation of 4% v/v THF in pH 2.54 0.1M KNO$_3$ in deionized water at 1.2 V vs. NHE. The proposed catalytic current for THF oxidation is the top most curve. A thinner working electrode was used to minimize the background from water oxidation shown by the middle trace.
Figure 15:
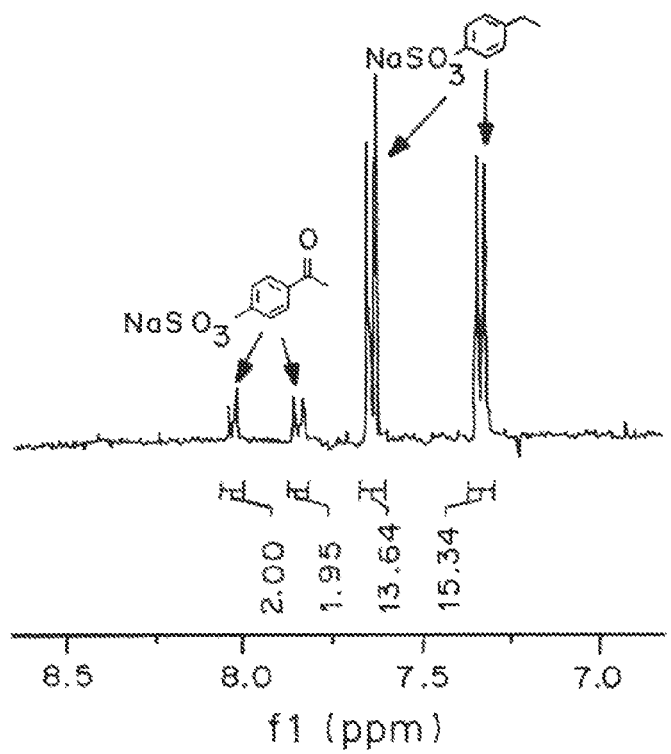
FIG. 15 is a section of an $^1$H NMR spectrum of a solution of ethylbenzene-sulfonate (EBS) oxidation at 1.2 V vs. NHE in acidic conditions for a total time of approximately 24 h, with peaks characteristic of the oxidation product, acetophenone-sulfonate (APS).
Figure 16:
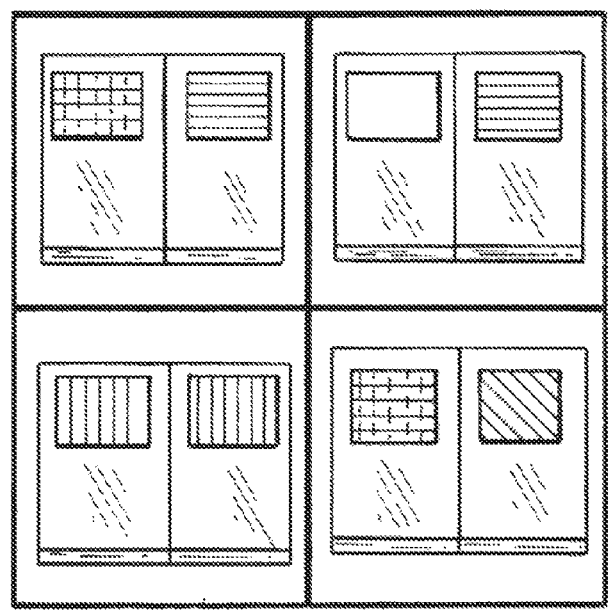
FIG. 16 are images of 1 cm$^2$ active areas of nanoporous ITO (top left), TiO$_2$ (top right), α-Fe$_2$O$_3$ (bottom left), and WO$_3$ (bottom right) on FTO/glass substrates. In each image, the sample on the left is pure oxide while the sample on the right has been coated with a monolayer of the molecular iridium catalyst.

The catalyst is also stable at higher potentials and catalytic current densities for prolonged times (>10 mA/cm$^2$, FIG. 13), which is particularly important for real world applications, such as water electrolysis. While water-oxidation is one of the primary applications of the catalysts, it may also be useful for other electrode-driven oxidation reactions. For instance, carbon-hydrogen bond oxidations are of particular interest because controlled electro-oxidations of liquid fuels, such as methanol to $CO_2$, are highly desirable for low-temperature fuel cell applications. Also, selective partial functionalization of hydrocarbons would be very useful for the upgrading of unreactive feedstocks, a process that can currently not be carried out electrochemically because of the lack of suitable catalysts. Preliminary experiments suggest that such conversions are possible, as shown below in FIGS. 14 and 15. FIG. 14 is chronoamperograms of tetrahydrofuran (THF) oxidation at 1.2 V vs. NHE. FIG. 15 is a $^1$H-NMR spectrum suggesting heterogeneous oxidation of ethylbenzene-sulfonate (EBS) to acetophenone-sulfonate (APS). FIG. 16 are images of 1 cm$^2$ active areas of nanoporous ITO (top left), $TiO_2$ (top right), α-$Fe_2O_3$ (bottom left), and $WO_3$ (bottom right) on FTO/glass substrates. In each image, the sample on the left is pure oxide while the sample on the right has been coated with a monolayer of the iridium catalyst.

Example 5. Heterogeneous Catalysts

Working Electrodes

Working electrodes for electrochemical characterization were constructed by spin-coating (Headway PWM32 Spin Coater, Headway Research Inc.) at 1000 rpm on 2.2 mm thick glass slides coated with 500 nm of fluorine-doped tin oxide (FTO, TEC 7, Hartford Glass Co. Inc.) for 30 seconds.

NanoITO (Sigma Aldrich, <50 nm particle size) was added to a mortar and pestle and ground for 10 minutes with glacial acetic acid. Ethanol was added to make a 5 M acetic acid/ethanol mixture, which was then sonicated for 10 minutes. A spin rate of 1000 rpm was used and the amount of nanoITO in the 5 M acetic acid/ethanol mixture as varied between 5 wt % and 30 wt % resulted in films having a thickness of between approximately 300 nm and 7 μm as measured by a profilometer after sintering (KLA Tencor Alphastep 200). Greater thicknesses were achieved by successive spin coating of additional layers beyond the first, heating the particles on a hot plate to 200° C. for 10 minutes between coatings. For example, an 18 μm thick film was produced by spin coating three successive layers of 6 μm thick films using a 27 wt % nanoITO in 5 M acetic acid/ethanol solution. No boundaries between spin coated layers were observed in SEM for the thicker films.

Heterogenization of the catalyst was as follows, with a 30 minute wait time between mixing the precatalyst and NaIO4 and immersion of the electrodes to ensure that no intermediate is being bound during its formation. The electrodes were immersed in a catalyst solution formed by oxidizing 10 mM Cp*Ir(pyalc)OH in 30 mL deionized water with 100 equivalents of NaIO$_4$. The electrodes were removed after two hours, washed thoroughly with deionized water, and had acquired a visible blue color. Side-by-side controls were used to measure the relative decrease in absorption of the catalyst solution, in order to approximately determine the amount of iridium that had adhered to the surface of the electrode. Electrochemical data were taken using 0.1 M $KNO_3$ in deionized water as an electrolyte, adjusted to pH 2.6 unless stated otherwise, with an Ag/AgCl reference electrode and Pt mesh counter electrode. Vigorous stirring was required in unbuffered solutions during long-term experiments to prevent etching of the nanoITO electrode under acidic conditions.

Long-term stability testing and oxygen detection using phase fluorometry were performed in a two-chamber electrochemical cell, with working and counter electrode chambers separated by a glass frit. For these experiments, such as is shown in FIG. 2c, low catalyst loading was achieved with 300-500 nm thickness nanoITO films on a 6.45 cm2 substrate, thereby minimizing pH effects due to the low buffer capacity of $KNO_3$ over the pH range studied. SEM and TEM data were taken both before and after electrolysis to determine that there were no changes to sample morphology and CVs were taken to ensure minimal loss of electroactive catalyst over the course of an experiment.

When preparing heterogeneous catalyst samples of Ir WOC, such as the catalyst bearing pyalc ligands, the absorption of the homogeneous catalyst solution at 580 nm was monitored after introduction of a substrate, with a control lacking nanoITO as a baseline. Fresh glassware must be used for each measurement due to the catalyst's ability to bind to numerous metal oxides, including SiO2. For electrochemical measurements mentioned in the text, electroactive iridium was used to gauge catalytic activity instead since it could be determined with higher accuracy using CV peak integration. Using both of these measurements, the ratio of electroactive Ir to Ir present on the surface detected by loss in absorption of the homogeneous catalyst solution during preparation was typically >90% (±5%). Electrochemical measurements were performed using a Princeton Applied Research Versastat 4-400 in a standard three electrode configuration, CVs were taken with a 5 second equilibration time at their starting potential prior to data collection.

For optical studies a Varian Cary 3 spectrophotometer with an integrating sphere attachment in absorption mode was used. A 6.45 cm$^2$ geometric surface area of nanoITO on FTO-coated glass was used in order to completely cover the aperture of the integrating sphere. A background spectrum was taken prior to immersion of the substrate into the homogeneous catalyst containing solution.

$TiO_2$ slides were prepared by doctor blading a paste containing ~21 nm $TiO_2$ nanoparticles (P25, Sigma Aldrich) prepared according to published methods on an FTO-coated glass slide, then heating in an oven to 450° C. in air for two hours. Heterogenization of $[Ir(pyalc)(H_2O)_2(\mu\text{-}O)]_2^{2+}$ on $TiO_2$ required only immersion of the substrate into the solution. A $WO_3$ paste for doctor blading onto an FTO-coated glass slide was made similarly to the nanoITO spin-coating paste, with 30 wt % $WO_3$ nanoparticles (<100 nm, Sigma Aldrich) in a 5 M acetic acid/ethanol mixture. After doctor blading onto an FTO-coated glass slide, the nanoparticles were heated in an oven to 550° C. in air for one hour. For attachment on $WO_3$, the pH of the homogeneous catalyst in solution was decreased to ~1.5 using a 1 M $HNO_3$ solution prior to immersion. The samples were allowed to sit for 12 hours (overnight) to ensure complete binding, then they were removed and washed thoroughly with deionized water.

Electrolyte pHs were adjusted using 1 M $HNO_3$ or 1 M KOH unless stated otherwise. An electrochemical cell was assembled in a quartz UV-Vis cuvette attached to an integrating sphere in a Shimadzu UV-2600 spectrophotometer. Standard electrolyte conditions of 0.1 M $KNO_3$ adjusted to pH 2.6 were used. Catalyst-coated nanoITO electrodes that were 6.45 cm long and 0.7 cm wide were prepared by cutting an FTO-coated glass slide with a 7 μm thick catalyst coated nanoITO film to the appropriate dimensions.

Working electrodes were constructed by attaching a copper wire to an exposed FTO surface on one side of the nanoITO coated FTO slide using conductive epoxy (Fast Setting Conductive Silver Epoxy, SPI). Six hours were allotted for the conductive epoxy to cure, then non-conductive water-resistant marine epoxy (White Marine Epoxy, Loctite, 24 hours allotted to cure) was applied on top of the conductive epoxy to prevent electrical contact between the wire leads and electrolyte, so that only the catalyst coated nanoITO was exposed. This was placed into the quartz cuvette along with Pt mesh counter and Ag/AgCl reference (BASi) electrodes adjacent to the integrating sphere, connected to a potentiostat (WavenowXV, Pine), and chronoamperometric experiments with various potentials were performed. The electrodes were given 3 minutes to stabilize at that potential, then a UV-Vis spectrum was taken using the integrating sphere in absorption mode. A blank nanoITO coated FTO slide without catalyst was used for a background scan.

The results are shown in FIGS. 17a-e. The blue-colored WOC binds to the electrode by $H_2O$ elimination, exhibiting an absorption maximum (λmax) at 580 nm as seen in FIG. 17a. Catalyst binding is rapid, self-limiting, and does not require any external driving force, such as photons or an electric potential applied to the electrode. Almost no further absorption changes are observed after two hours of immersion at room temperature (FIG. 17b), indicating formation of a molecular monolayer. Even after thorough rinsing with deionized water, the blue species is not washed off. Scanning electron microscope (SEM) images of the electrode indicate that no nanoparticulate deposits are formed, and energy-dispersive x-ray spectroscopy (EDX) measurements confirm the presence of iridium on the electrode surface without any traces of iodine or sodium from the chemical oxidant used to produce the catalyst.

Figure 17D:
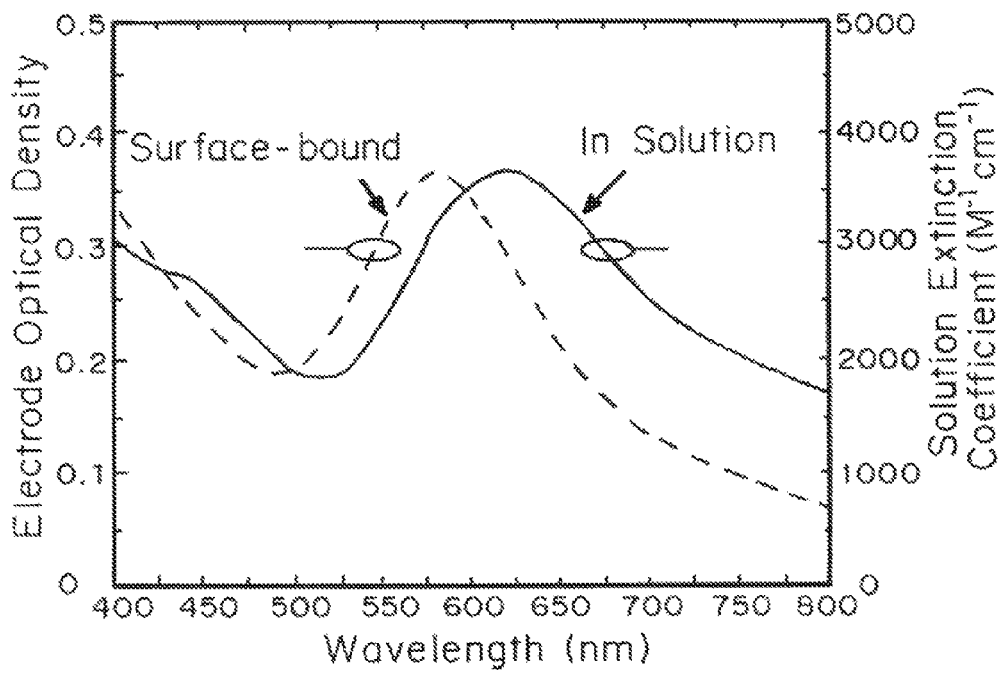
FIG. 17d is a graph comparing the spectra for the catalyst on the surface (red) to the catalyst in solution (blue).
Figure 17E:
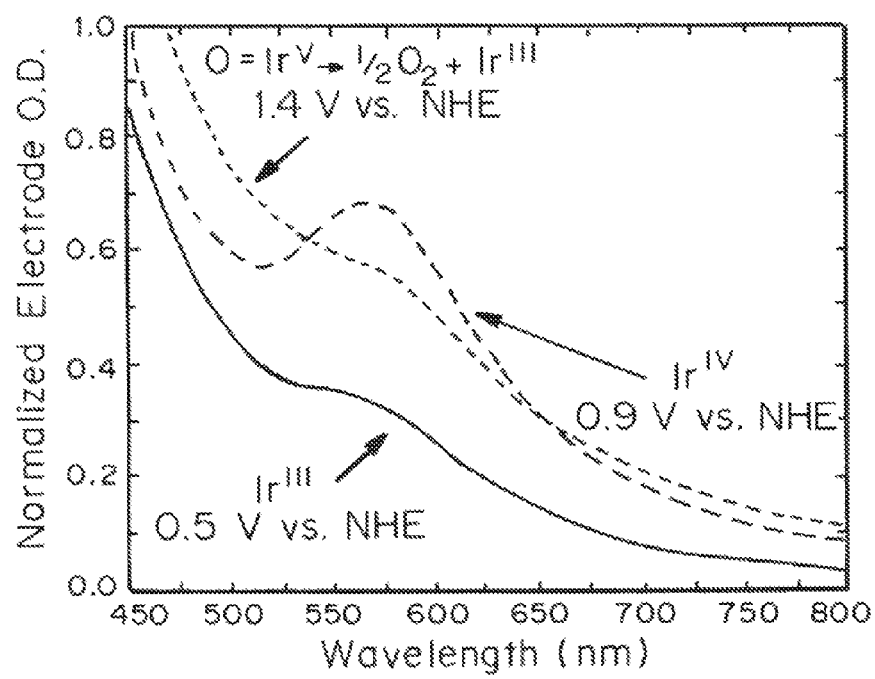
FIG. 17e is a graph showing the spectroelectrochemical response of the electrode showing reversible transitions between Ir$^{III}$, Ir$^{IV}$, and proposed catalytically active Ir$^V$ states. The absorption feature at 580 nm is characteristic of Ir$^{IV}$.

The catalyst's absorbance peak maximum blue-shifts from 608 nm in solution to 580 nm upon binding to nanoITO (FIG. 17d). This shift is similar to that previously observed for the reversible deprotonation of bound water ligands. Along with the fact that the catalyst remains bound to the surface after repeated washing, this suggests that there is a change in catalyst structure upon surface immobilization, implying chemical binding rather than mere physisorption. This peak shift is still evident after the electrode is immersed in aqueous solution in a spectroelectrochemical cell (FIG. 17e). In this experiment, the catalyst-coated nanoITO working electrode forms a circuit with an Ag/AgCl reference electrode and a platinum counter electrode. The potential applied to the working electrode was varied to induce reversible changes in the oxidation state of iridium in the catalyst while collecting UV-Vis spectra. Importantly, the catalyst remains bound to the electrode not only in its native $Ir^{IV}$ state, but also in its reduced $Ir^{III}$ oxidation state, as well as the catalytically active putative $Ir^{V}$ state from which oxygen evolution is observed.

The stability and versatility of the surface-bound WOC is shown by its irreversible adhesion in both acidic and basic aqueous solutions (pH values ranging from 1-12) and in numerous organic solvents. Only repeated washing under highly alkaline conditions (pH>13) was found to remove the catalyst, thereby resulting in a clean electrode surface. The catalyst also adheres rapidly to different nanostructured metal oxides that are commonly used as photoanodes for water oxidation, including $TiO_2$ and $WO_3$. More fascinating attributes, however, are its high activity and stability on a conductive electrode surface during electrochemical water oxidation.

Oxygen Detection and Faradaic Yield

Headspace oxygen detection was performed using a Tau-Theta MFPF-100 kHz phase fluorometric oxygen detection system with a FOSPOR-R probe (Ocean Optics). The experiment was performed in a custom-built two chamber gas-tight electrochemical cell. A sample made for long-term electrolysis was constructed using conductive epoxy to secure a wire to bare FTO on a 6.45 $cm^2$ geometric surface area FTO-coated glass slide covered with a nanoITO film<300 nm thick. The conductive epoxy was then coated with white marine epoxy. The two-chamber cell was fitted with an Ag/AgCl reference electrode in the working electrode chamber and a Pt electrode in the counter electrode chamber and filled with pH 2.6, 0.1 M $KNO_3$ in deionized water. The FOSPOR-R probe was inserted into a rubber septum that was secured on one of the apertures in the working electrode chamber of the electrochemical cell, and all connections lacking an O-ring were wrapped tightly with Parafilm and electrical tape. Both chambers were degassed under vigorous stirring with high purity $N_2$ for over 2 hours using needles inserted into rubber septa bubbling through the electrolyte solution, while monitoring oxygen content to ensure that $O_2$ in the system was minimal. The needles were then removed and the purge was stopped, and $O_2$ levels were monitored for 30 minutes with no increase in $O_2$ concentration to ensure a stable, oxygen-free atmosphere had been achieved.

Oxygen was detected with a Clark electrode using a custom made zero-headspace 10 mL glass cell, water jacketed for constant temperature. A Teflon cap through which the Clark electrode membrane contacted deionized water (adjusted to pH 2.5 using nitric acid) also held a catalyst-coated nanoITO film on FTO-coated glass sample that was submerged in the cell. Catalyst-loaded samples were prepared similarly to those used for electrochemistry, except with a 1.6 $cm^2$ geometric surface area. The Clark electrode was allowed to stabilize while stirring the deionized water solution for one hour prior to injection with an oxidizing solution of freshly prepared $NaIO_4$ in deionized water. Catalyst response and $O_2$ generation occurred immediately, without any lag phase.

A typical experiment, used 25 μL of 0.25 M $NaIO_4$ in deionized water. The oxygen content in the cell was monitored until oxygen evolution ceased, which for a loading of around 50 nmol of iridium (corresponding to a nanoITO film 11 μm thick) took approximately 90 minutes. Data were collected while stirring the solution to ensure steady state oxygen readings. A sample was used that was loaded with approximately 49.1 nmol of iridium. Decreasing the amount of catalyst on the surface by decreasing nanoITO thickness, higher turnover numbers and turnover frequencies were achieved. This is likely due to both a larger ratio of oxidant to catalyst and a higher percentage of the catalyst easily accessible to the solution without having to diffuse oxidant through the mesoporous nanoITO film.

A constant overpotential of 520 mV was applied for two hours. Bubble formation on the working and counter electrodes was immediately visible upon applying the potential.

Vigorous stirring was necessary in order to prevent bubble accumulation on the surface of the working electrode. This did cause some oxygen bubbles to become trapped near the glass frit or the O-ring holding the working electrode chamber together, causing a lag time between $O_2$ bubble generation and detection in the headspace. The volume of gas in the headspace of the working electrode chamber was measured to be 38 mL. CVs were taken both before and after electrolysis with little change, showing minimal loss of catalyst over the course of the experiment. By integration of the $Ir^{III}/Ir^{IV}$ redox wave, total electroactive iridium was determined to be ~0.66 nmol. This corresponds to approximately 7.9 (±0.6) turnovers of $O_2$ per second per iridium atom, and a turnover number of 56,800. Faradaic yield was calculated to be 98.7%. No significant current or oxygen generation was found at the same potential from a similar nanoITO on FTO-coated glass electrode without the pyalc Ir WOC on the surface as a control.

The heterogenized WOC maintains its activity for oxygen evolution with chemical oxidants (FIG. 18a) compared with that previously observed for the analogous homogeneous WOC in solution. Most importantly, however, the heterogenized WOC shows exceptional activity when driven electrochemically. Cyclic voltammograms (CVs) in an oxygen-saturated solution of 0.1 M $KNO_3$ in water at pH 2.6 (FIG. 18c) show reversible $Ir^{III}/Ir^{IV}$ charging features with E1/2=0.75 V vs. NHE, as well as reversible water oxidation/oxygen reduction similar to iridium oxides, but lacking a redox feature that has been assigned to the oxidation of IrIV to IrV. The onset of the water-oxidation catalytic wave occurs at a distinctively lower potential than the IrIV/IrV redox couple in IrOx samples prepared by different means, and thereby obscures the IrIV/IrV charging feature. This is a direct result of this catalyst's low overpotential for water oxidation, which can be partially attributed to the high electroactivity of the molecular iridium compound on the surface. Specifically, integration of the IrIII/IrIV wave demonstrates that >90% of iridium on the electrode is electroactive.

The surface-bound catalyst also shows excellent stability, and is capable of sustaining water oxidation for many hours at a 250 mV overpotential without degradation (FIG. 18d), reaching turnover numbers (TON) in excess of 106 $O_2$ molecules evolved per iridium atom over multiple trials. Moving to higher applied potentials (+520 mV relative to thermodynamic) we measure a turnover frequency (TOF) of 7.9 s-1 $O_2$ molecules evolved per electroactive iridium atom, which is higher than any previously reported value for iridium systems, and a 99% Faradaic yield for $O_2$ evolution is measured using a phase fluorometric oxygen sensor. The observed high performance further distinguishes this molecular iridium WOC from bulk iridium oxides.

Figure 18A:
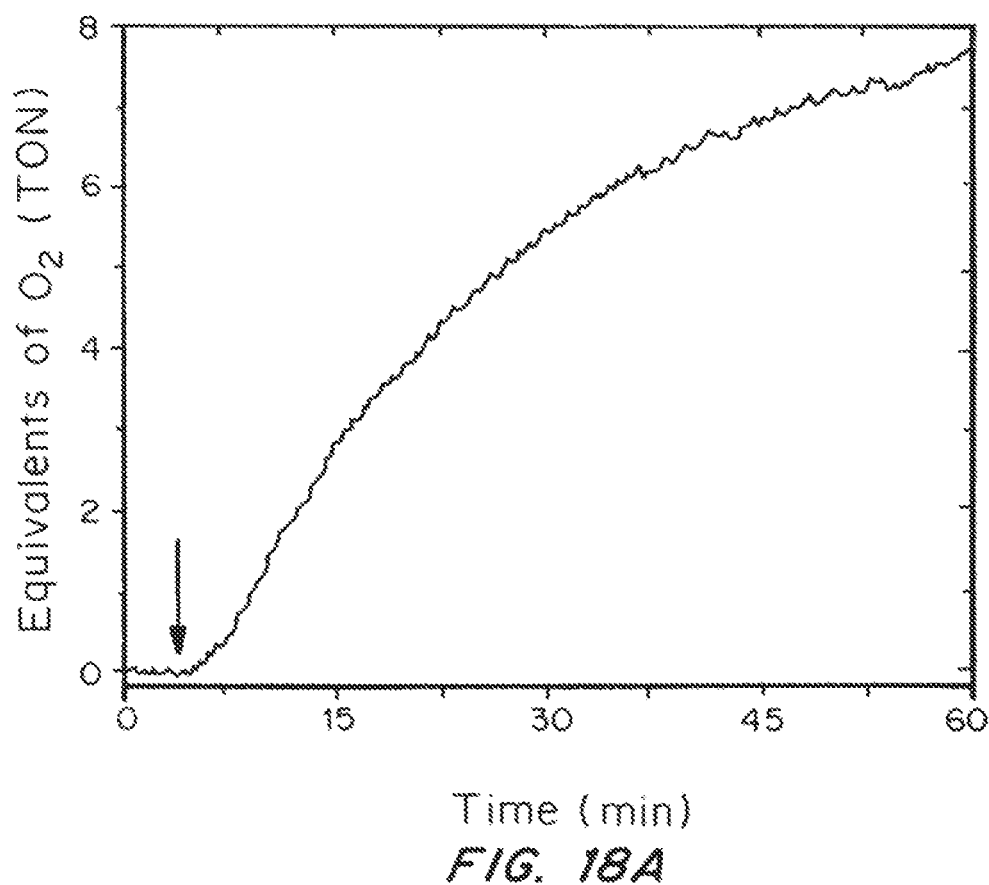
FIG. 18a is a graph showing water oxidation using NaIO$_4$ as a sacrificial oxidant with the catalyst bound to nanoITO; the arrow corresponds to injection of NaIO$_4$ solution, initiating catalysis.
Figure 18B:
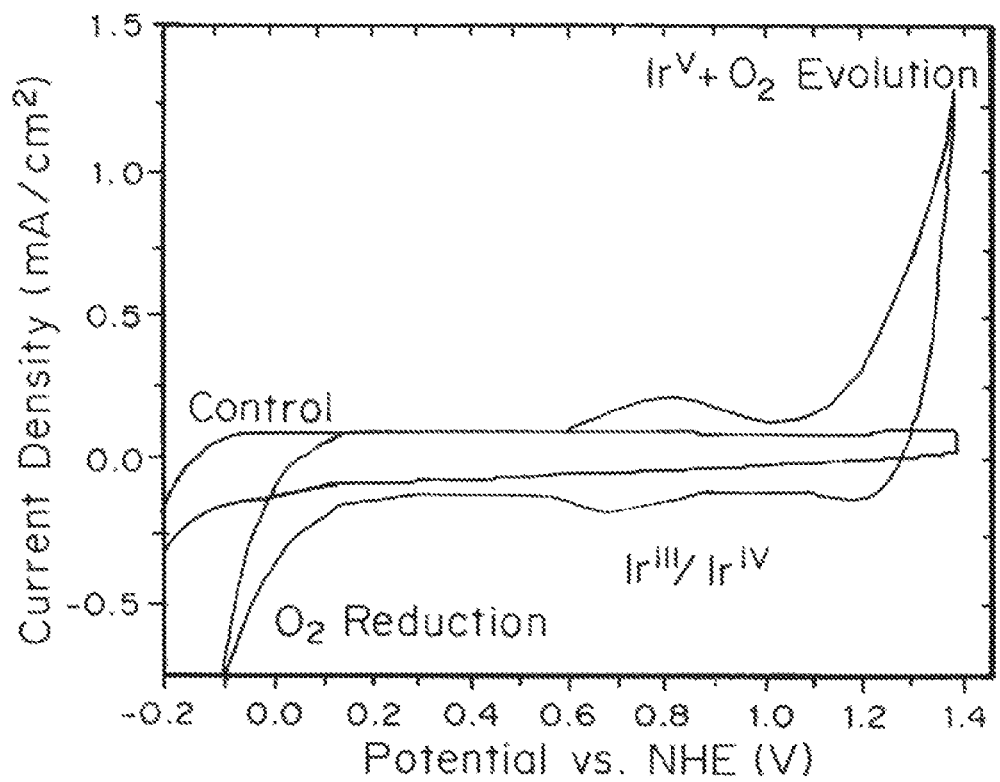
FIG. 18b is a cyclic voltammogram of a catalyst loaded nanoITO electrode compared to a similar nanoITO electrode without catalyst in an oxygen-saturated solution of 0.1 M KNO$_3$ in water at pH 2.6, taken with a 10 mV/s scan rate.
Figure 18C:
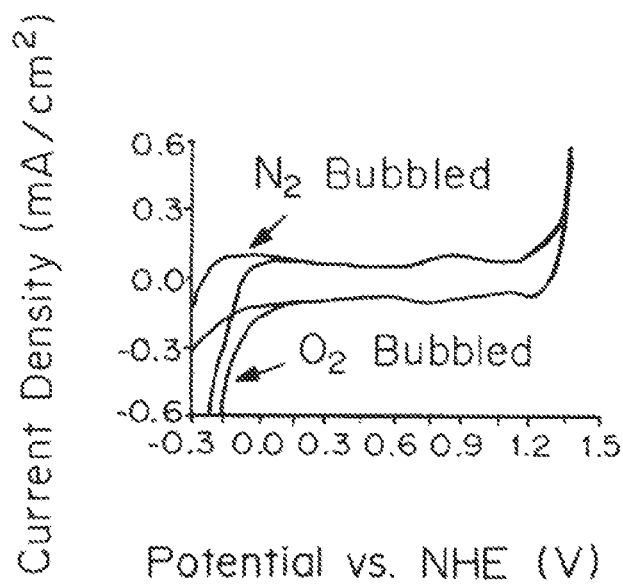
FIG. 18c shows the effect of saturating O$_2$ or N$_2$ gas in solution when using thinner electrodes, highlighting the catalytic wave for oxygen reduction at 0 V vs. NHE.
Figure 18D:
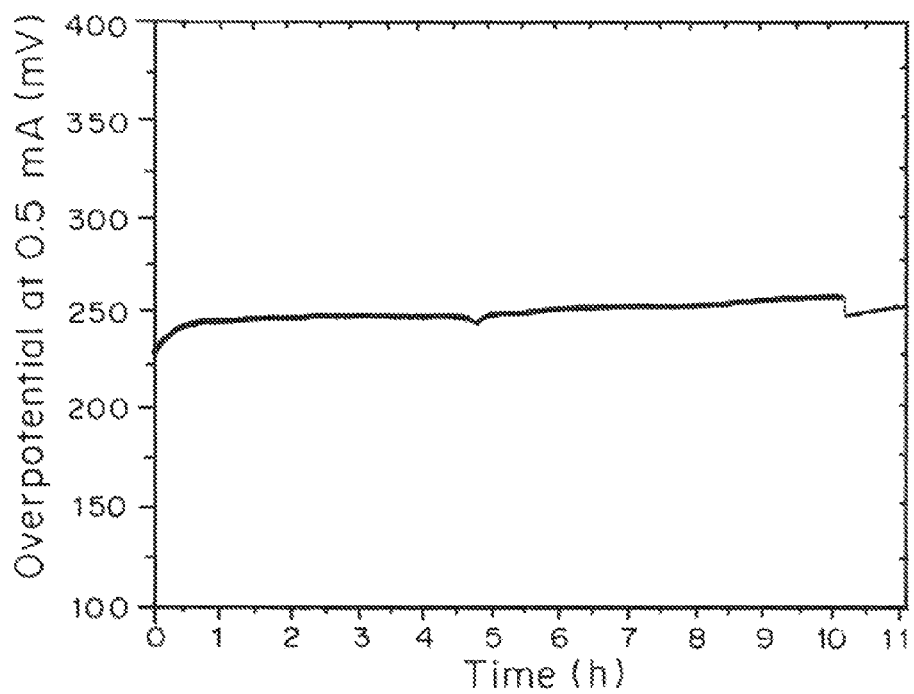
FIG. 18d is a graph showing the stability of the catalyst during water oxidation over 11 hours. Small increases and decreases correspond to bubble formation and release, which was minimized by rapidly stirring the solution.
Figure 18E:
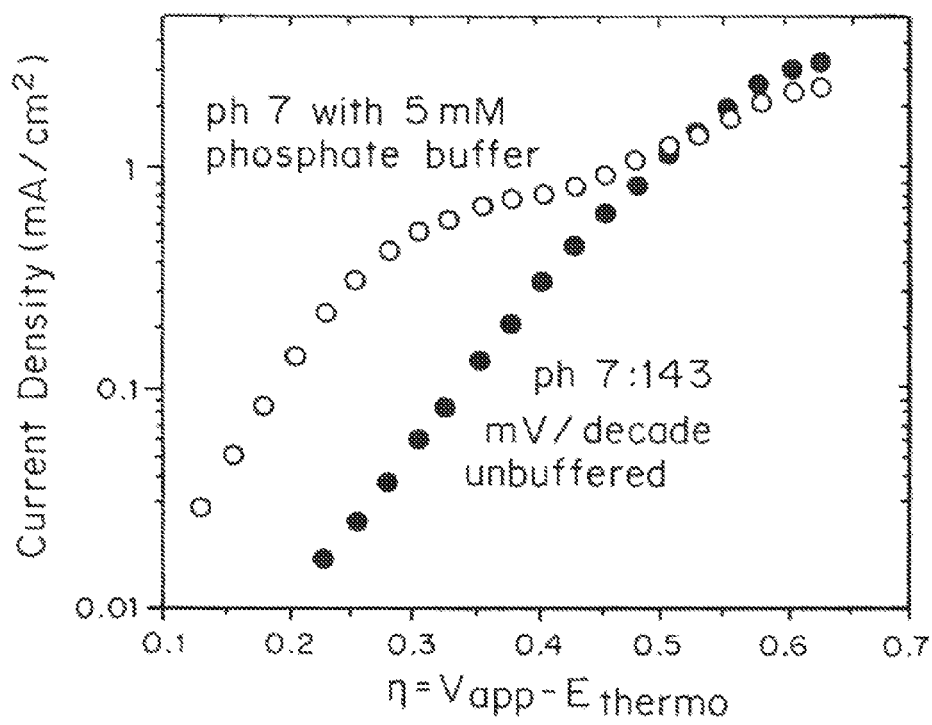
FIG. 18e is a Tafel plot at pH 7 showing the effect of adding a phosphate buffer to the 0.1 M KNO$_3$ solution.
Figure 18F:
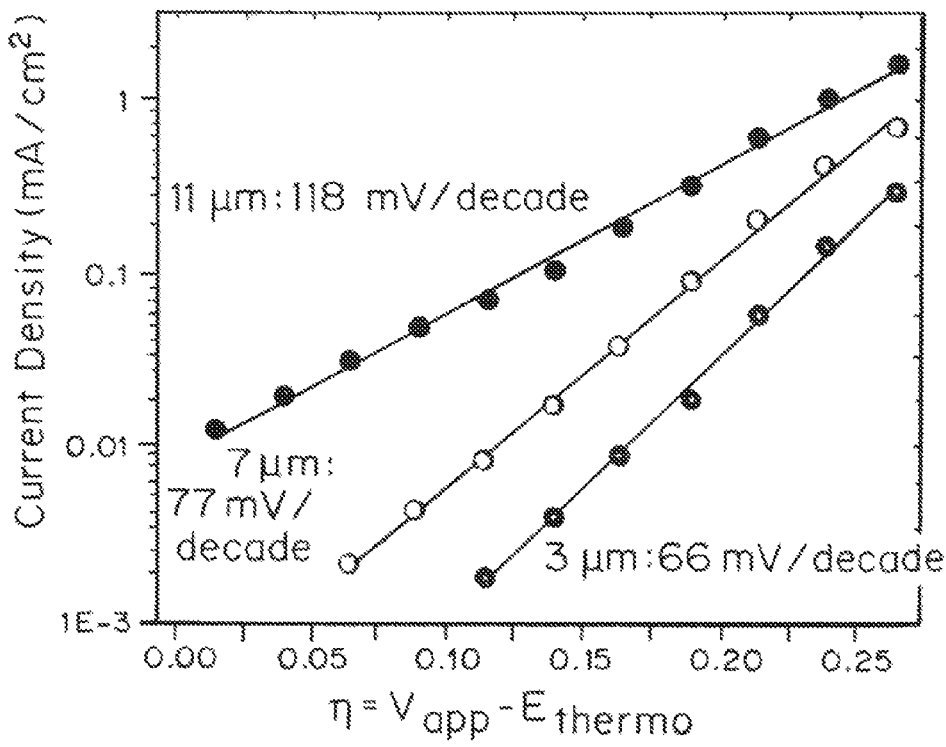
FIG. 18f is Tafel plot at pH 2.6 without any added buffer. A decrease in Tafel slope (Δη/Δ log(i)) with decreasing film thickness corresponds to a decrease in diffusion-related pH effects.

Tafel plots of catalytic currents were made over a range of pH and buffer conditions (FIG. 18e) and with electrodes of varying thickness of the porous nanoITO film to increase catalyst loading by increasing the electrode surface area (FIG. 18f). Limitations on proton diffusion through the nanoporous films on electrodes caused a decrease in measured activity due to the low buffering capacity of $KNO_3$ at pH 7. As thicker nanoITO films were used, the pH gradient formed through the film decreases electrode performance over time regardless of the catalyst's stability, because the locally generated highly acidic conditions etch the ITO support. At low applied potentials, adding a buffer such as phosphate is beneficial; however, as the applied potential is increased, activity decreases presumably due to phosphate coordination to iridium in the catalyst. Identical behavior occurs with amorphous $IrO_x$. Along with similarities in their pH dependence, CVs, and spectroelectrochemical measurements, these results support the hypothesis that the active catalytic sites in these iridium oxides are mechanistically similar to this surface-bound molecular species. Using a pH of 2.6, where pH is less sensitive to proton production from water oxidation, Tafel slopes increase as nanoITO film thickness is increased since protons generated from water oxidation must diffuse through a thicker film.

Figure 11A:
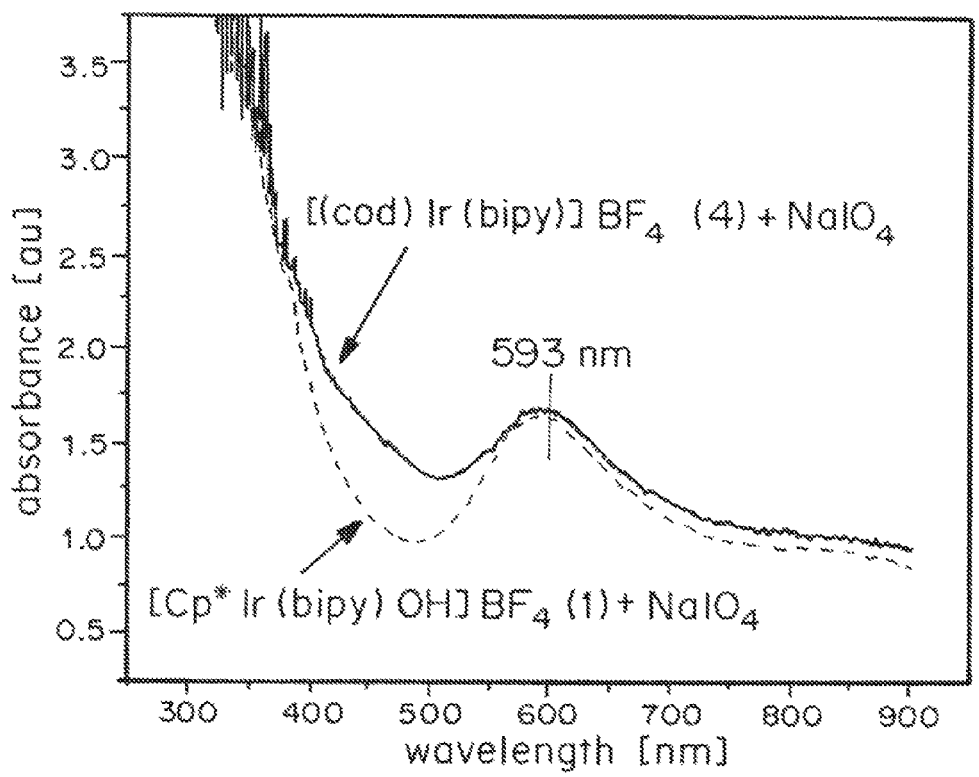
FIGS. 11A and 11B are UV-Vis spectra of different Ir-precursors (1 mM) 30 minutes after oxidation with NaIO$_4$ (100 mM) in water, demonstrating that different precursors with various placeholder ligands may be used to generate the same active species.
Figure 11B:
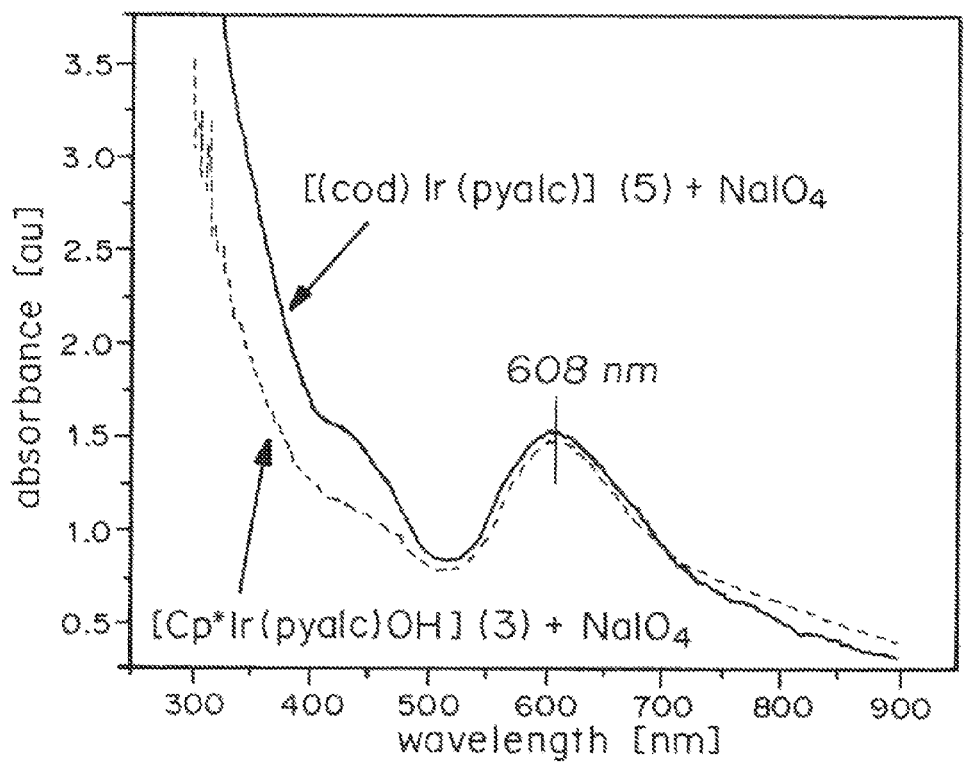

Remarkably, however, as seen in FIG. 18f 11 μm thick samples have high enough catalyst loading to allow sustained current densities with an onset of linearity in the Tafel plot beginning at overpotentials as low as 14 mV (where the current density is 11 μA/cm2). This is consistent with the onset of water oxidation (Ecat) for this catalyst being at nearly the thermodynamic potential.

Figure 18G:
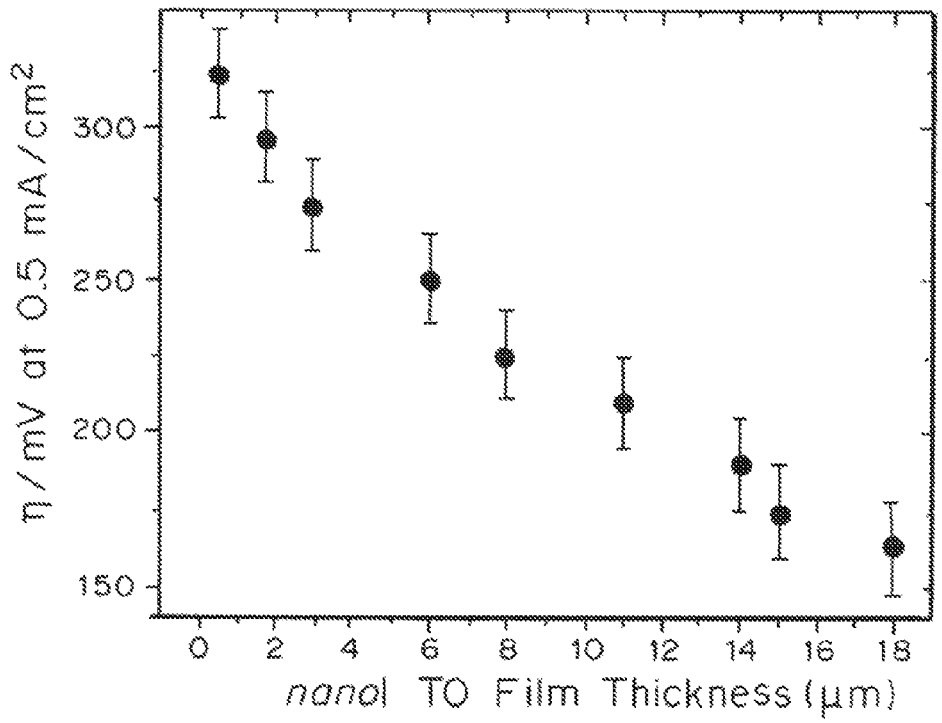
FIG. 18g is a graph showing electrode overpotential as a function of catalyst loading on the electrode, the overpotential required in order to reach 0.5 mA/cm$^2$ decreases as catalyst loading increases. Catalyst loading on the electrode was varied by using different thicknesses of the spin-coated nanoITO substrate. Data were gathered using 5 minute dwell times to allow electrodes to adequately stabilize.

By increasing the nanoporous film thickness, the overpotential of the electrode at specific current densities can be decreased (FIG. 18g). For example, typical 3 μm thick nanoITO films require an overpotential of 275 mV to attain a catalytic current of 0.5 mA/cm2, whereas 18 μm thick films require less than 160 mV. Lower overpotential values have not been reported in the literature for this current density. Controlling electrode overpotential by tuning catalyst loading with scaffold surface area provides another advantage to using well-defined surface-bound molecular catalysts for water oxidation.

Figure 19B:
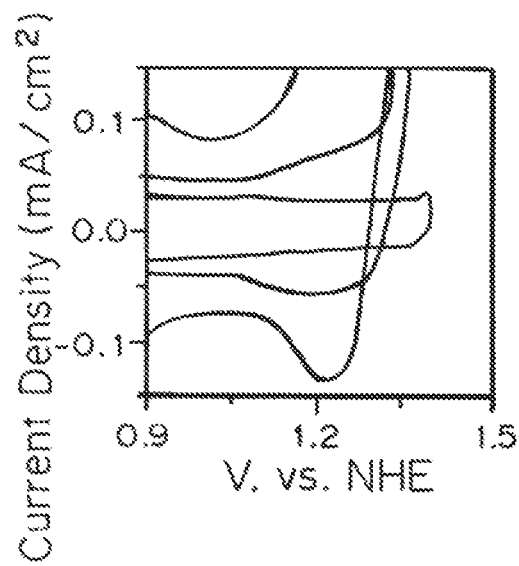
FIGS. 19a and 19b are cyclic voltammograms taken with a 10 mV/s scan rate at pH 2.6 of catalyst coated nanoITO electrodes as prepared and heated to different temperatures.
Figure 19A:
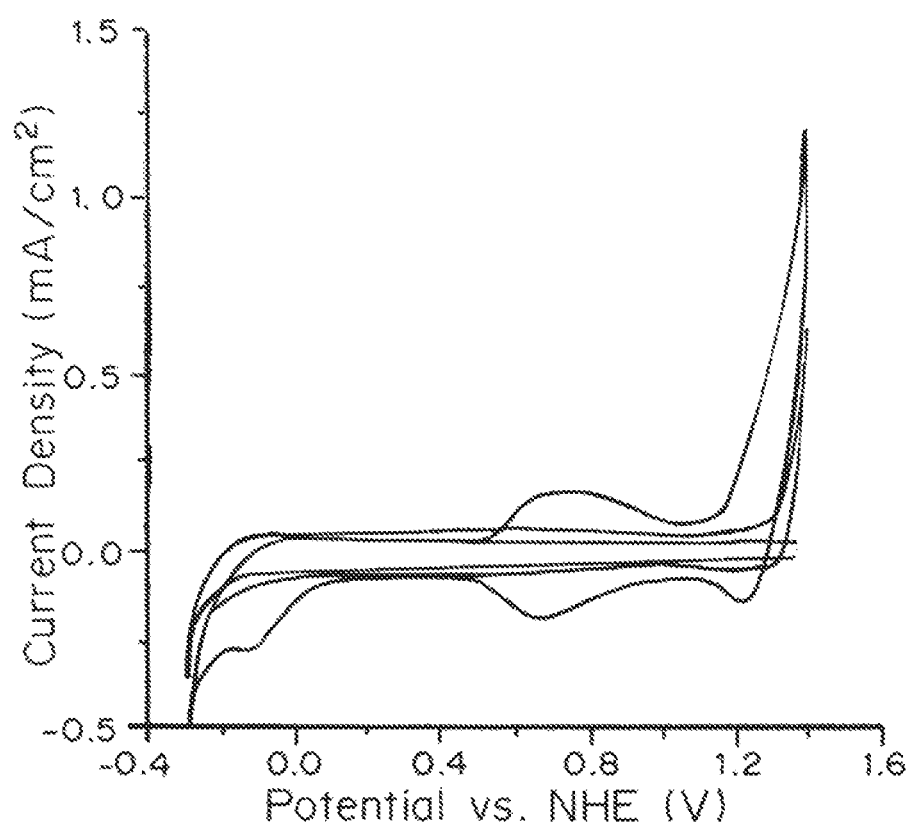

To further probe the molecular nature of this heterogenized water-oxidation catalyst, the catalyst was compared with iridium oxide-based materials formed by heating an as-prepared electrode to 500° C. or 700° C. for one hour (FIG. 19a). Scanning transmission electron microscope analysis coupled with EDX mapping (STEM-EDX) displays the nanoscale coverage of iridium on ITO nanoparticles. As deposited, there is a highly conformal coating of iridium on each particle, consistent with a surface-bound molecular species. The corresponding CV has a catalytic wave for water oxidation beginning at 1.1 V vs. NHE (1.25 V vs. RHE). Heating an electrode covered with the molecular catalyst at 500° C. in air burns off the pyalc ligand without affecting conformal coating of iridium oxide around each ITO nanoparticle. This causes an anodic shift in the catalytic wave for water oxidation to 1.3 V vs. NHE, revealing a feature at 1.1 V vs. NHE typically assigned to the IrIV/IrV redox couple; in the unheated sample, the catalytic wave for water oxidation obscures this feature. Heating an electrode coated with the molecular catalyst to 700° C. in air results in the formation of crystalline rutile $IrO_2$ clusters with ~20 nm diameter. In accordance with literature precedence, these show comparatively less activity in part because most of the iridium is no longer in contact with water, reducing the number of active surface sites.

The homogeneous and heterogeneous catalysts exhibit extremely low overpotentials compared to the prior art at the point of catalysis for a specific current flow. For example, surface-bound heterogeneous catalysts show sustained current flow that increases linearly beginning at overpotentials of 15-20 mV for water oxidation, which corresponds to $E_{cat}$=1.25 V vs RHE, which is over an order of magnitude lower than the prior art as shown in the table (adapted from Smith, R. D. L. et al., Science (2013) 340(6128):60-63) below

| | $E_{cat}$ (V vs. RHE)) |
|---|---|
| α-FeO$_x$ | 1.55 ± 0.02 |
| α-CoO$_x$ | 1.44 ± 0.02 |
| α-NiO$_x$ | 1.42 ± 0.01 |
| α-FeCoO$_x$ | 1.41 ± 0.01 |
| α-FeNiO$_x$ | 1.44 ± 0.01 |
| α-FeCoNiO$_x$ | 1.42 ± 0.01 |
| α-CoP$_i$* | 1.51 |
| α-NiB$_i$† | 1.53 |
| α-MnO$_x$ | 1.59 |
| LaNiO$_3$‡ | 1.38 |
| Co$_3$O$_4$‡ | 1.40 |
| RuO$_2$‡ | 1.36 |
| IrO$_2$‡ | 1.44 |

*Phosphate,
†Borate,
‡Crystalline phases

The energy required for catalysis ($E_{cat}$ in the table) using the catalysts is 110 mV lower than the prior art catalysts.

Figure 20:
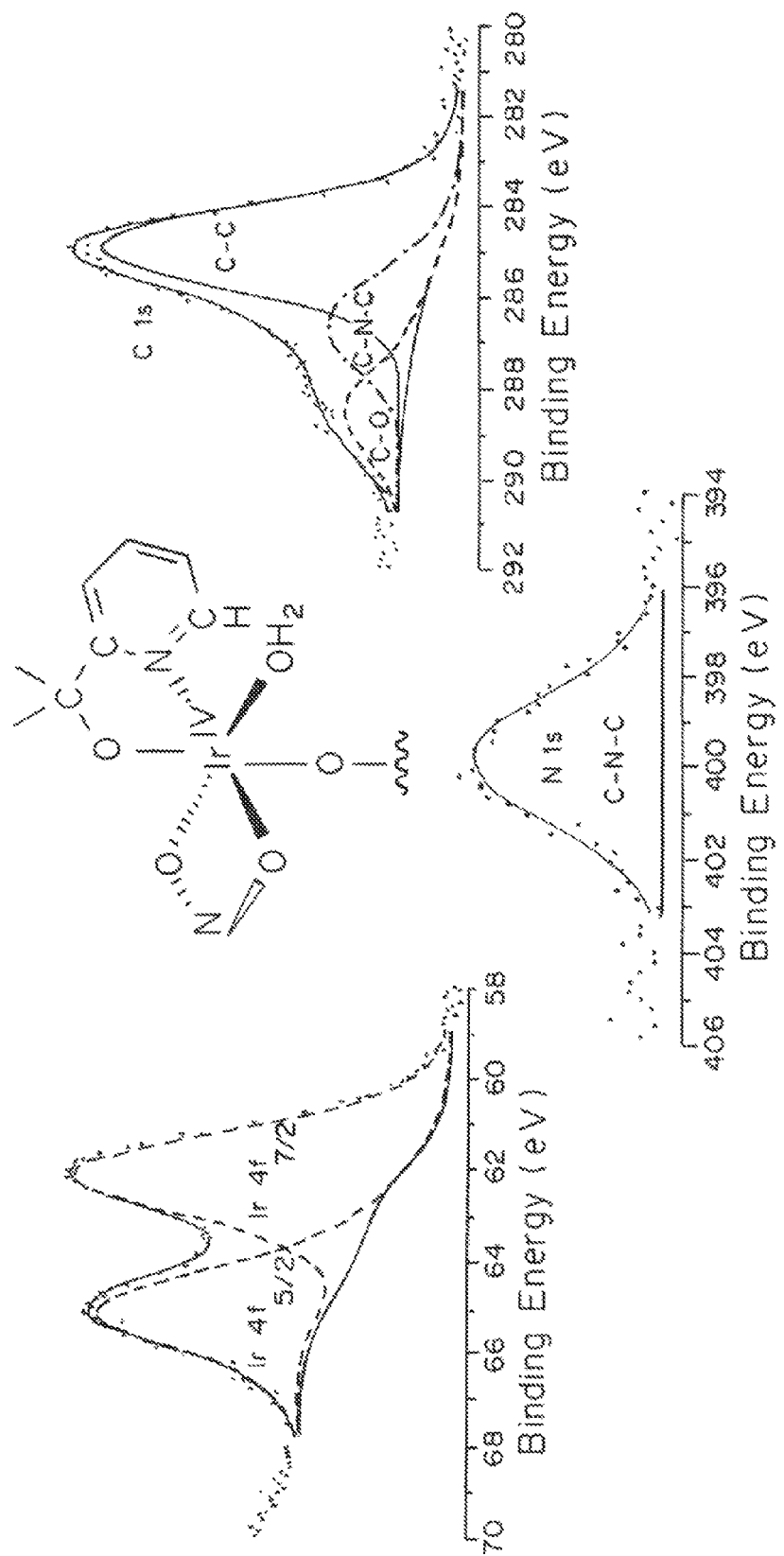
FIG. 20 are X-ray photoelectron spectra taken after 16 hours of water-oxidation catalysis. Signals corresponding to the iridium (left), nitrogen (bottom, middle) and carbon (right) show that both the metal and ligand are still intact after prolonged electrolysis. No changes are observed before and after electrolysis.

The oxidatively resistant bidentate pyalc ligand bound to iridium in this molecular heterogeneous compound represents a striking difference between it and traditional iridium oxide materials. Therefore, it is important to show that the ligand remains after extended periods of electrolysis, demonstrating that the surface-bound molecular species is stable. X-ray photoelectron spectroscopy (XPS) of an electrode used for approximately 16 hours of electrolysis shows that the pyalc ligand remains after more than 100,000 turnovers of O$_2$ per iridium atom (FIG. 20).

Lastly, an often-cited advantage of molecular catalysts is their tunability, and this system is no exception. By changing the bidentate chelating ligand in the homogeneous catalyst before deposition on the electrode surface, the properties of the surface-functionalized electrode are drastically changed. If, for example, 2,2'-bipyridine is used to form a proposed [Ir(bpy)(H$_2$O)$_2$(μ-O)]$_2$n$^+$ compound in solution, a semitransparent yellow iridium compound is deposited with electrochemical properties that are very distinct from those of the blue pyalc-derived catalyst, and much lower oxygen evolution activity is observed.

This demonstrates an effective heterogenization strategy for homogeneous catalysts with preservation of their molecular tunability.

Figure 21:
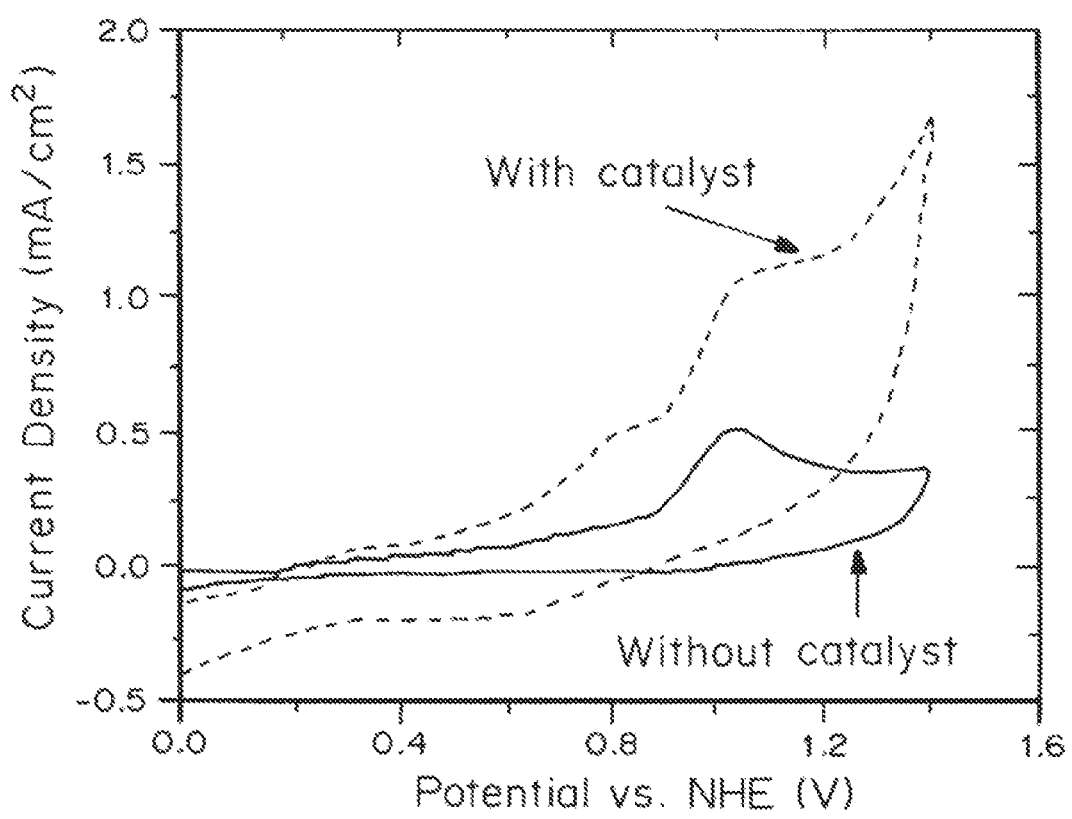
FIG. 21 depicts the electrochemical behavior of glassy carbon which has been coated with the iridium catalyst compared with glassy carbon which has not.

Example 6. Ir$^{IV}$ Catalyst Binds to Glassy Carbon without External Stimulus The iridium catalysts disclosed herein binds to other substrates by simple immersion for a few hours at room temperature without any other external stimulus as demonstrated on conductive carbon fiber cloth. The catalyst bound to this carbon-based material exhibits very high electrocatalytic activity in water-oxidation. A working electrode of [Ir(pyalc)(H2O)$_2$(mu-O)]$_2$$^{2+}$ bound to a conductive carbon fiber cloth under sustained water-splitting conditions at 1.4 V vs. NHE produced visible bubbles of evolved oxygen, and in a CV shows forward and reverse waves for the reversible Ir$^{III}$/Ir$^{IV}$ redox event and a catalytic wave for water oxidation, both not present in a control sample without the surface-bound catalyst present. See FIG. 21

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention. Such equivalents are intended to be encompassed by the following claims.

We claim:

1. A compound of Formula (I)

$$\{[Ir(LX)_x(H_2O)_y(\mu\text{-}O)]_z^{m+}\}_n \qquad (I),$$

wherein x, y, m are integers independently selected from 0, 1, 2, 3, and 4, z is an integer selected from 1, 2, 3, and 4, n is an integer selected from 2 and 4, and LX is an oxidation-resistant chelate ligand.

2. The compound of claim 1, wherein x is 1-2, y is 1-2, m is 1-2, and z is 1-2.

3. The compound of claim 1, wherein x is 1, y is 2, m is 2, and z is 1 or 2.

4. The compound of claim 1, wherein z=2.

5. The compound of claim 4, wherein LX is selected from the group consisting of 2-(2-pyridyl)-2-propanolate, 2,2'-bipyridine; 2-phenylpyridine, picolinate and combinations thereof.

6. The compound of claim 1, wherein LX is a monodentate, bidentate, or tridentate ligand.

7. The compound of claim 6, wherein LX is one or more N-heterocyclic carbenes, pyridines, alkoxides, carboxylates, amides, phosphine oxides, and amino alkoxides.

8. The compound of claim 6, wherein LX is 2(2-pyridyl)-2-propanolate.

9. The compound of claim 6, wherein LX is 2,2'-bipyridine.

10. A method for reducing organic species by electrolysis, the method comprising contacting the organic species to be reduced with the compound of claim 1.

11. A method for reducing oxygen to water in an electrochemical fuel cell, oxygen detector or oxygen scavenging device, the method comprising contacting oxygen with the compound of claim 1.

12. A method of making the compound of Formula (I):

$$\{[Ir(LX)_x(H_2O)_y(\mu\text{-}O)]_z^{m+}\}_n \qquad (I),$$

wherein x, y, m are integers independently selected from 0, 1, 2, 3, and 4, z is an integer selected from 1, 2, 3, and 4, n is an integer selected from 2 and 4, and LX is an oxidation-resistant chelate ligand, comprising:

oxidizing a compound of Formula (II)

$$(PHL)Ir(LX)(OH)_w \qquad (II),$$

wherein LX is an oxidation-resistant chelate ligand, PHL is a placeholder ligand, and w is an integer selected from 0, 1, 2 and 3.

13. The method of claim 12, wherein the compound of Formula (II) is selected from the group consisting of [(PHL)Ir(LX)OH], [(PHL)Ir(LX)], and combinations thereof.

14. The method of claim 12, wherein the placeholder ligand comprises pentamethylcyclopentadienyl, cyclopentadienyl, phenylcyclopentadienyl, indenyl, (meth)allyl, 1,5-cyclooctadiene, 2,5-norbornadiene, cyclooctene, ethylene, and carbon monoxide.

15. A system comprising a substrate and a compound of Formula (I)

$$\{[Ir(LX)_x(H_2O)_y(\mu\text{-}O)]_z^{m+}\}_n \qquad (I),$$

wherein x, y, m are integers independently selected from 0, 1, 2, 3, and 4, z is an integer selected from 1, 2, 3, and 4, n is an integer selected from 2 and 4, and LX is an oxidation-resistant chelate ligand wherein the compound of Formula (I) is preparable by a method comprising:

oxidizing a compound of Formula (II)

$$(PHL)Ir(LX)(OH)_w \quad (II),$$

wherein LX is an oxidation-resistant chelate ligand, PHL is a placeholder ligand, and w is an integer selected from 0, 1, 2 and 3.

16. The system of claim 15, wherein the compound is in the form of a monolayer bonded to the surface of the substrate.

17. The system of claim 16, wherein the monolayer is physically and chemically stable.

18. The system of claim 17, wherein the catalyst retains its catalytic activity.

19. The system of claim 15, wherein the compound of Formula (II) is selected from the group consisting of [(PHL)Ir(LX)OH], [(PHL)Ir(LX)], and combinations thereof.

20. The system of claim 15, wherein the placeholder ligand comprises pentamethylcyclopentadienyl, cyclopentadienyl, phenylcyclopentadienyl, indenyl, (meth)allyl, 1,5-cyclooctadiene, 2,5-norbornadiene, cyclooctene, ethylene, and carbon monoxide.

21. The system of claim 15, wherein the substrate comprises one or more allotropes of carbon, metal oxide, mixed-metal oxide, conductive polymers or combinations thereof.

22. The system of claim 21, wherein the one or more allotropes of carbon is selected from carbon fiber, glassy carbon, carbon wool, graphene, amorphous carbon, nanotubes, and mixtures thereof.

23. The system of claim 21, wherein the metal oxide, mixed metal oxide, or both are a conductive oxide.

24. The system of claim 23, wherein the conductive oxide is tin-doped indium oxide.

25. The system of claim 21, wherein the metal oxide, mixed metal oxide, or both are a photocatalytic oxide.

26. The system of claim 25, wherein the photocatalytic oxide is selected from the group consisting of titanium dioxide, iron oxide, tungsten trioxide, and combinations thereof.

27. A method of performing an oxidation, the method comprising contacting a compound of Formula (I)

$$\{[Ir(LX)_x(H_2O)_y(\mu\text{-}O)]_z^{m+}\}_n \quad (I),$$

wherein x, y, m are integers independently selected from 0, 1, 2, 3, and 4, z is an integer selected from 1, 2, 3, and 4, n is an integer selected from 2 and 4, and LX is an oxidation-resistant chelate ligand;

with an oxidizable substrate.

28. The method of claim 27, wherein the oxidizable substrate is water.

29. The method of claim 27, wherein the oxidizable substrate contains an oxygen-hydrogen, carbon-hydrogen, and/or nitrogen-hydrogen bond, wherein the oxygen-hydrogen, carbon-hydrogen, and/or nitrogen-hydrogen bond is oxidized.

30. The method of claim 27, wherein the oxidizable substrate is a halide ion.

31. The method of claim 27, wherein the oxidizable substrate is organic waste material.

32. The method of claim 27, wherein the contacting is carried out in the presence of a chemical oxidant, an electrochemical potential, or electromagnetic radiation.

33. A method of depositing iridium oxide on a substrate, the method comprising combining a compound of Formula (I):

$$\{[Ir(LX)_x(H_2O)_y(\mu\text{-}O)]_z^{m+}\}_n \quad (I),$$

wherein x, y, m are integers independently selected from 0, 1, 2, 3, and 4, z is an integer selected from 1, 2, 3, and 4, n is an integer selected from 2 and 4, and LX is an oxidation-resistant chelate ligand, or a compound of Formula (II)

$$(PHL)Ir(LX)(OH)_w \quad (II),$$

wherein LX is an oxidation-resistant chelate ligand, PHL is a placeholder ligand, and w is an integer selected from 0, 1, 2 and 3, with a substrate under conditions suitable to deposit iridium oxide.

34. The method of claim 33, wherein the conditions suitable to deposit iridium oxide include heat, electromagnetic radiation or strong acid.

35. The method of claim 33, wherein the iridium oxide is reduced to iridium metal.

* * * * *